(12) United States Patent
Dedo et al.

(10) Patent No.: US 7,326,227 B2
(45) Date of Patent: *Feb. 5, 2008

(54) TOURNIQUET PADDING

(75) Inventors: Richard G Dedo, Hillsborough, CA (US); Stephanie Bohrer, Lakewood, WI (US)

(73) Assignee: Richard G. Dedo, Hillsborough, CA (US)

( * ) Notice: Subject to any disclaimer, the term of this patent is extended or adjusted under 35 U.S.C. 154(b) by 486 days.

This patent is subject to a terminal disclaimer.

(21) Appl. No.: 10/226,829

(22) Filed: Aug. 23, 2002

(65) Prior Publication Data
US 2003/0065357 A1 Apr. 3, 2003

Related U.S. Application Data

(63) Continuation-in-part of application No. 09/795,606, filed on Feb. 28, 2001, now Pat. No. 6,537,298.

(51) Int. Cl.
*A61B 17/00* (2006.01)

(52) U.S. Cl. ................ 606/203; 604/289; 604/290; 128/132

(58) Field of Classification Search ............... 606/201, 606/202, 203, 204; 604/290; 602/13, 202; 128/677
See application file for complete search history.

(56) References Cited

U.S. PATENT DOCUMENTS 4,302,495 A 11/1981 Marra .................. 428/110

(Continued)

OTHER PUBLICATIONS

Galls Inc., *Galls—Product Details; Disposable Blanket*, 1 page (2002) www.galls.com/firehouse/shop/viewProductDetail.jsp?item=EMO42 (printed Jan. 9, 2002).

(Continued)

*Primary Examiner*—Michael J. Hayes
*Assistant Examiner*—Victor Nguyen
(74) *Attorney, Agent, or Firm*—Whyte Hirschboeck Dudek SC

(57) ABSTRACT

Tourniquet padding and methods of its use with a tourniquet are provided. The tourniquet padding comprises a cover sheet with at least one surface having anti-slip properties, and can be made with and without a compressible padding material disposed on the cover sheet. The tourniquet padding has a length sufficient to be wrapped around a limb of a person, and a width wider than the tourniquet. The cover sheet can be gathered along the proximal edge to accommodate a range of circumferences of extremities, and include an elastic member for wrapping around the extremity. The surface of the cover sheet to be placed in contact with the skin can include one or more adhesive elements to provide an interrupted adhesive surface. The adhesive elements can comprise an adhesive material that is adherable to skin, or a frictionally adhesive material having anti-slip properties to maintain the padding device in place on the skin during use. The surface of the cover sheet can comprise a liquid-repellent material to protect the tourniquet from becoming wet or soiled during a medical procedure. In an embodiment of the tourniquet padding, a padding material is disposed on a cover sheet such that at least the distal edge portion of the cover sheet can be turned onto a tourniquet disposed on the padding material. In another embodiment, the cover sheet comprises an extension of material along the lower or distal edge having an adhesive surface that is applied to the skin, and a second layer that is turned proximally over the lower (distal) edge of the tourniquet to protect the tourniquet, and to keep it from slipping distally.

In use, the tourniquet padding is wrapped about an extremity, a tourniquet is positioned onto the padding material, and the distal edge portion of the cover sheet is turned onto the tourniquet and secured. The distal edge portion of the cover sheet can include perforations to divide it into sections. As the tourniquet inflates and deflates, the cover sheet overlying the tourniquet flexes to accommodate the change in thickness. The tourniquet padding maintains a blood pressure cuff or other tourniquet in place on a limb and prevents it from slipping down the extremity during use.

40 Claims, 17 Drawing Sheets

U.S. PATENT DOCUMENTS

| | | | | |
|---|---|---|---|---|
| 4,348,444 A | | 9/1982 | Craig | 428/137 |
| 4,406,281 A | * | 9/1983 | Hubbard et al. | 128/846 |
| 4,422,837 A | | 12/1983 | Rasmussen | 425/289 |
| 4,762,123 A | * | 8/1988 | Dedo | 128/898 |
| 4,820,279 A | | 4/1989 | Dedo | 604/290 |
| 4,834,802 A | * | 5/1989 | Prier | 606/203 |
| 5,180,359 A | * | 1/1993 | Dedo | 602/6 |
| 5,212,001 A | | 5/1993 | Brant et al. | 428/34.9 |
| 5,411,518 A | * | 5/1995 | Goldstein et al. | 606/202 |
| 5,413,582 A | | 5/1995 | Eaton | 606/202 |
| 5,569,693 A | | 10/1996 | Doshi et al. | 524/317 |
| 5,617,707 A | | 4/1997 | Simmons | 53/441 |
| 5,690,672 A | * | 11/1997 | Cohen | 606/203 |
| 5,733,304 A | | 3/1998 | Spence | 606/203 |
| 5,823,012 A | | 10/1998 | Hacskaylo | 2/170 |
| 5,901,706 A | | 5/1999 | Griesbach et al. | 128/849 |
| 5,922,441 A | | 7/1999 | Eichbauer | 428/213 |
| 5,968,072 A | | 10/1999 | Hite et al. | 606/202 |
| 6,022,617 A | | 2/2000 | Calkins | 428/354 |
| 6,027,465 A | | 2/2000 | Scholz et al. | 602/6 |
| 6,028,017 A | | 2/2000 | Curtin et al. | 442/370 |
| 6,041,443 A | | 3/2000 | Pas et al. | 2/239 |
| 6,100,206 A | | 8/2000 | Scholz et al. | 442/42 |
| 6,132,835 A | | 10/2000 | Scholz et al. | 428/68 |
| 6,171,681 B1 | | 1/2001 | Mascarenhas et al. | 428/141 |
| 6,265,055 B1 | | 7/2001 | Simpson et al. | 428/213 |
| 6,332,825 B1 | | 12/2001 | Henricksen | 450/81 |
| 6,361,548 B1 | | 3/2002 | McEwen | 606/201 |
| 6,537,298 B2 | * | 3/2003 | Dedo | 606/203 |

OTHER PUBLICATIONS

Little Rapids Corporation, *Little Rapids Corporation—Engineered Materials*, 2 pages, www.littlerapids.com/em/markets.html (printed Jan. 9, 2002).

Little Rapids Corporation, *Graham Dental Products—Dental Bibs*, 5 pages, www.littlerapids.com/graham/dental/products/dental_bibs.shtml (printed Jan. 9, 2002).

Little Rapids Corporation, *Graham Medical Table Rolls*, 6 pages; www.grahammedical.com/page1.shtml (printed Jan. 9, 2002).

Little Rapids Corporation, *Graham Medical—Towels and Washcloths*; 4 pages, www.grahammedical.com/page6.shtml (printed Jan. 9, 2002).

Ashlon, LLC, *Ashlon, LLC—Dental Bib, MEDICOM—Dental Bib, 13×18 Yellow—dental disposable . . .* , 1 page (1999), http://www.ashlon.com/item.jhtml (printed Jan. 9, 2002).

Georgia-Pacific Corporation, *Georgia-Pacific Away-From-Home-Products—Nonwovens*, 1 page (1997-2001); www.gp.com/awayfromhome/products/nonwovens.html (printed Jan. 9, 2002).

Georgia-Pacific Corporation, *Georgia-Pacific Away-From-Home Products—Airlaid Fabrics*, 1 page (1997-2001) www.gp.com/awayfromhome/products/nonwovens—airlaid.html (printed Jan. 9, 2002).

Georgia-Pacific Corporation, *Georgia-Pacific Away-From-Home Products—Carded Fabrics*, 1 page (1997-2001), www.gp.com/awayfromhome/products/nonwovens—carded.html (printed Jan. 9, 2002).

BASF Aktiengesellschaft, *BASF AG: Dispersions: Product Groups: Nonwovens and Coatings: Nonwoven fabrics*, 1 page (1999), www.basf.de/en/dispersionen/products/nonwovens/fabrics/ (printed Jan. 9, 2002).

BASF Aktiengesellschaft, *BASF AG: Dispersions: Product Groups: Nonwovens and Coatings: Nonwoven fabrics: H . . .* , 1 page (1999), www.basf.de/en/dispersionen/products/nonwovens/fabrics/hygiene/ (printed Jan. 9, 2002).

BASF Aktiengesellschaft, *BASF AG: Dispersions: Product Groups: Nonwovens and Coatings: Nonwoven fabrics: H . . .* , 2 pages (1999), www.basf.de/en/dispersionen/products/nonwovens/fabrics/hygiene/products/ (printed Jan. 9, 2002).

* cited by examiner

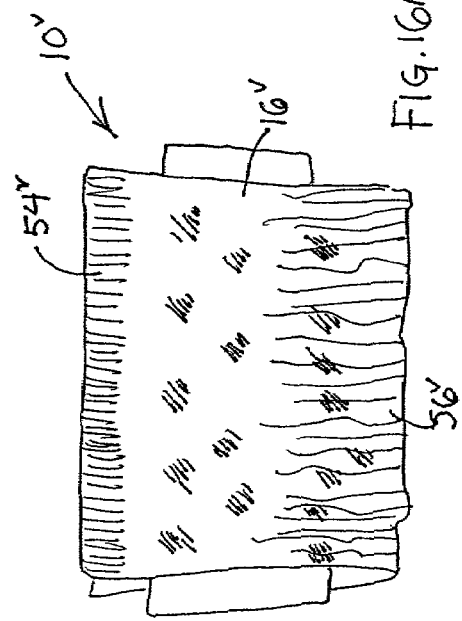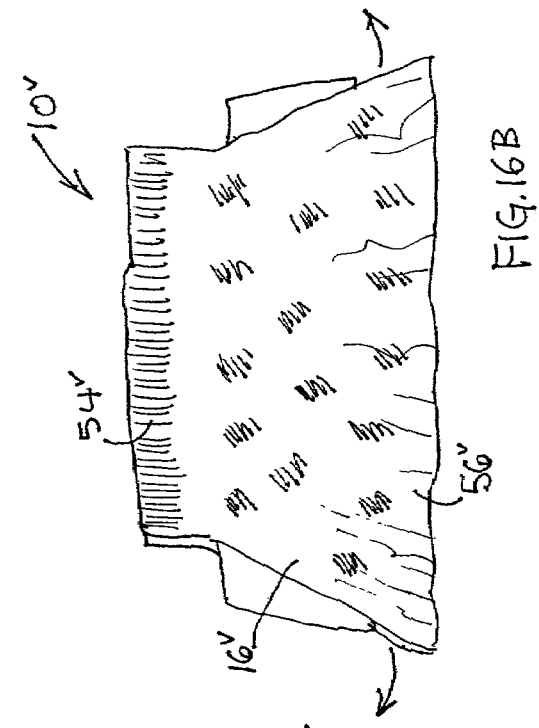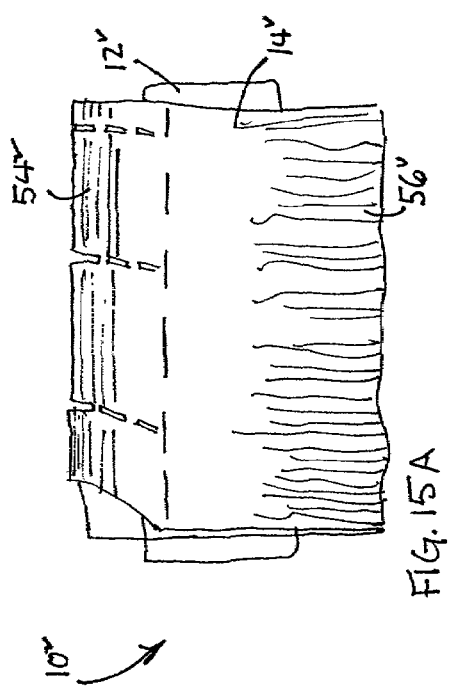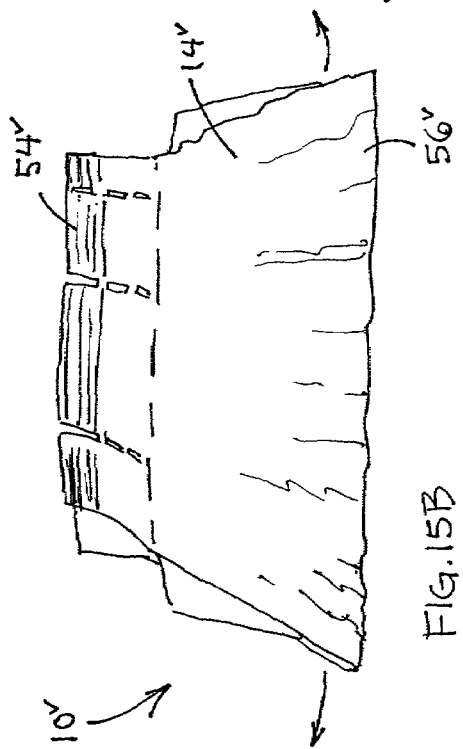

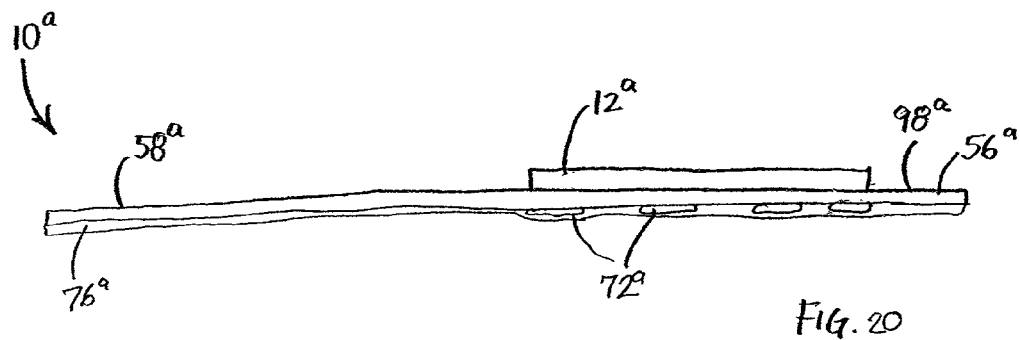
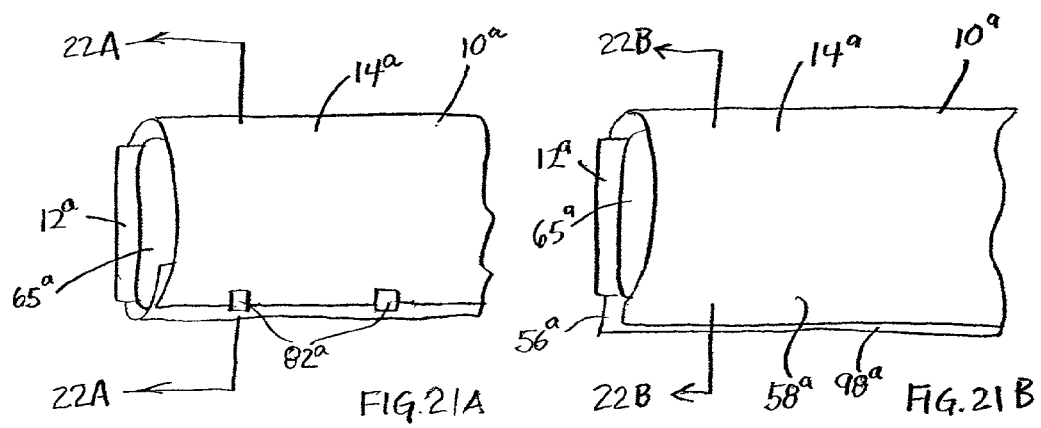
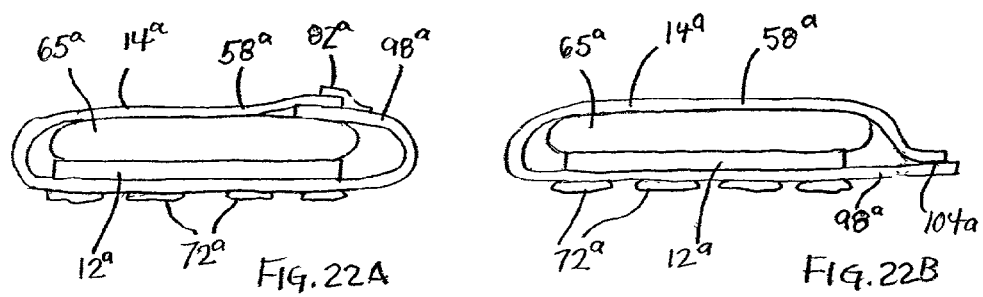

TOURNIQUET PADDING

CROSS-REFERENCE TO RELATED APPLICATIONS

This application is a continuation-in-part of U.S. patent application Ser. No. 09/795,606, filed Feb. 28, 2001 now U.S. Pat. No. 6,537,298.

FIELD OF THE INVENTION

The present invention relates to disposable padding for use in the medical field, and more particularly to padding used in connection with blood pressure cuffs and other tourniquets.

BACKGROUND OF THE INVENTION

Tourniquets are used by orthopedists, anesthesiologists and other medical practitioners to stop the flow of blood through an artery by compression, and are typically placed proximally on an upper or lower extremity such as the upper arm or thigh, and occasionally in a more distal position such as on the calf. Inflatable tourniquet cuffs are commonly used in the medical field, and include bladders that are inflated by compressed air, producing enough compression to occlude the arterial flow. For an orthopedist or other surgeon who does extremity surgery, this achieves an avascular, or "non-bleeding," dry surgical field. By stopping the flow of blood into the extremity, surgery can be performed in that extremity distal to the tourniquet without bleeding. With the artery occluded, no blood flows into the surgical field and the surgeon can perform surgery in what is temporarily an avascular area.

To completely stop the flow of blood, a tourniquet should be applied as high as possible into the axilla or "armpit" in an upper extremity, or into the groin adjacent to the inguinal ligament located at the crease between the lower abdomen and the anterior, or front part of the top of the thigh. Such placement occludes the artery before it begins to divide into its branches, and provides a surgeon with a large operative field for elbow and knee surgery. A large area is needed in order to prep the skin adequately and to drape the area properly so that during surgery, if an incision needs to be extended, the surgeon does not need to cut through drapes to do so.

Tourniquets in the form of blood pressure cuffs, are also used by anesthesiologists to monitor blood pressure during surgical procedures, by nurses in intensive care units, by medical personnel in transitional care units, among others. A blood pressure cuff is often applied and left on for an extended time period, i.e., several days. The cuff is applied as high as possible on the upper extremity in order to more effectively occlude the artery before it branches and obtain a more accurate blood pressure measurement.

In use during a surgical procedure, a tourniquet is applied with continuous pressure for an extended period of time. In the use of a blood pressure cuff during a surgical procedure or in an intensive care or cardiac care unit, the cuff is automatically and repeatedly inflated and deflated at about one to two minute intervals to monitor blood pressure, and can be left on for several days. This adds up to numerous compressions of the skin during a procedure or treatment period.

Tourniquets are commercially available and typically 2 to 6 inches wide for single bladder tourniquets and about 8 to 9 inches wide for double bladder tourniquets ("Bier blocks"). A blood pressure cuff about 4 inches wide is used most frequently by anesthesiologists. For an average size patient, a 4-inch wide tourniquet is used for upper extremity surgery, while a 4- to 6-inch wide tourniquet is typically applied to the thigh for surgeries on the lower extremities.

Tourniquets are generally supplied without padding, and some surgeons and anesthesiologists use a tourniquet without padding underneath. However, this can result in injury to the skin caused by prolonged or intermittent pinching while the surgery is performed or when the blood pressure tourniquet is inflated/deflated to monitor blood pressure.

To avoid skin irritation and damage to the outer layers of the skin by the repeated compression, a soft padding material is typically wrapped around the extremity and the tourniquet is applied over the wrapped material. Typically, 3 to 4 layers of sheet wadding or cast padding such as WEBRIL™ cotton padding (Kendall Company) are used under the tourniquet.

Although desirable, the use of padding under a tourniquet is problematic. The diameter or circumference of the upper arm and thigh decreases from the proximal end (i.e., shoulder, hip) to the distal end (i.e., elbow, knee). In most people, the upper arm and thigh are conically shaped like an ice cream cone, being wider at the top and narrowing toward the elbow or knee. This presents problems in maintaining a tourniquet in a stationary position on the upper part of the arm or the upper part of the thigh. Although the cushioning effect of the padding is a plus, the padding tends to slip distally down the extremity during a procedure. This situation becomes more problematic as the weight of the person increases and the distal part of the extremity is proportionately smaller than the proximal part. In addition, a heavier patient tends to have looser skin and subcutaneous tissues, requiring a higher amount of compression to occlude the artery for surgery or to obtain blood pressure.

Slippage of a blood pressure cuff along a limb causes particular problems for anesthesiologists and surgeons. For surgical procedures, the tourniquet cuff is applied to the upper arm and inflated, blood pressure is recorded, and the cuff is then deflated. As this is repeated over an extended time during the procedure, the cuff slips distally and a different part of the extremity becomes compressed. This change in the location where the blood pressure measurements are taken can result in inaccurate readings.

There have also been numerous complaints about tourniquet slippage down the arm or thigh and causing problems with proper occlusion of the artery during surgical procedures. For a surgical operation performed on an elbow, knee, forearm, hand, calf or foot, as the tourniquet slips distally, compression decreases and compromises the surgical field with bleeding. In addition, the distal edge of the tourniquet is not sterile, and as the edge enters the surgical field, the potential for post-operative infection increases. There have also been problems with the tourniquet or cuff slipping off the underlying padding material onto the skin, resulting in blisters where the skin had been pinched.

Another problem arises when the tourniquet is applied over several layers of cast padding, and the limb is prepped with a wet surgical scrub. An extremity is typically elevated while it is being prepped by a scrub nurse, and fluid that runs up the arm or leg wets the tourniquet and/or tourniquet padding. Most surgical preps include skin irritants and are applied and then wiped or rinsed off the skin. Consequently, compression by a wet padding and prolonged contact with a pre-operative skin prep can result in serious damage to the outer layers of the skin.

In addition, tourniquets that become soiled with blood or other fluids are difficult to clean thoroughly and, in cases of AIDS and other infectious diseases, the contaminated tourniquet is usually discarded. With the cost of tourniquets at about $200 and higher, this can significantly increase the cost of a surgery or other medical procedure.

Therefore, it would be desirable to provide a padding that can be used in connection with a blood pressure cuff and other tourniquets that overcome the foregoing problems.

SUMMARY OF THE INVENTION

The present invention provides a tourniquet padding designed to deal with the foregoing problems of anesthesiologists and surgeons who use tourniquets.

In one aspect, the invention provides a tourniquet padding for use with a tourniquet. In one embodiment, the tourniquet padding comprises a cover sheet with at least one surface having anti-slip properties. Preferably, the tourniquet padding further includes a compressible material disposed on a surface of the cover sheet.

In an embodiment of the tourniquet padding, the surface of the cover sheet to be placed in contact with the skin comprises one or more adhesive elements to provide an interrupted adhesive surface. The adhesive elements can comprise an adhesive material that is adherable to skin such as a pressure-sensitive adhesive material, or a frictionally adhesive material such as silicon rubber, latex rubber, or foamed polyvinyl chloride, having anti-slip properties to maintain the padding device in place on the skin. The tourniquet padding has a length sufficient to be wrapped around a limb of a person, and a width wider than the tourniquet. The cover sheet can comprise an extension of material along the lower or distal edge having an adhesive surface that is applied to the skin, and a second layer that is turned proximally over the lower (distal) edge of the tourniquet to protect the tourniquet, and to keep it from slipping distally. In another embodiment, a compressible padding material is secured on one side of a material layer with the other side having one or more adhesive elements disposed thereon to provide a non-slip surface. A tourniquet is placed onto the tourniquet padding, and the distal edge of the material layer is turned onto the tourniquet and secured using an adhesive element. The present tourniquet padding advantageously holds a blood pressure cuff or other tourniquet in place on a limb and prevents it from slipping down the limb during use.

In yet another embodiment, the tourniquet padding comprises a compressible material disposed on a single- or multi-layer stretch cling polymeric film. The tourniquet padding is wrapped around the extremity, with the film-side of the padding applied against the skin. The film possesses elongation properties, and a moderate to high level of cling to prevent slippage of the tourniquet padding along the extremity during use. The film layer can be formed from a polymeric resin having inherent cling performance properties, or a polymeric resin incorporating a tackifying or cling agent. Additionally, adhesive elements can be applied to the surface of the film layer to be applied to or disposed against the skin of the user.

The portion of the tourniquet padding to be turned proximally onto the tourniquet can include perforations or slits provided at suitable intervals (along the length) that allow it to be divided or split to accommodate a range of sizes of tourniquets, and/or the inflation/deflation of the tourniquet during use. In another embodiment, the tourniquet padding may be crimped, pleated or otherwise gathered along a proximal edge to make it slightly elastic, in order to accommodate extremities (arm/leg) of varying circumferences. An elastic member can also be attached along the proximal edge portion to further secure the tourniquet padding to an extremity.

In a preferred embodiment, the tourniquet padding also includes a layer of plastic or other liquid-repellent material to cover the distal edge and at least a portion of the outer surface of the cover sheet that is placed against the skin. This protects the padding from becoming soaked by prep solutions and other liquids that are applied to the limb.

In another aspect, the invention provides methods for using the tourniquet padding with a blood pressure cuff or other tourniquet. In one embodiment using a tourniquet padding having a contact surface with discrete adhesive areas, the tourniquet padding is wrapped around a limb of a person and the adhesive areas are applied to or disposed against the skin. A tourniquet is then positioned over the tourniquet padding and wrapped around the limb such that the distal edge of the tourniquet padding extends beyond the distal edge of the tourniquet. The cover sheet of the tourniquet padding is adhered to or brought into frictional contact with the skin, and the distal edge portion is folded onto the tourniquet and secured in place, for example, by adhering it to the tourniquet, or by securing the distal edge portion to the proximal edge portion of the cover sheet, among other methods. The distal edge portion of the cover sheet can include perforations or slits to separate the edge portion into sections that are folded onto the tourniquet. The tourniquet can then be inflated and deflated as required by the medical procedure.

In another embodiment of the method, a tourniquet padding comprising a stretch cling (non-slip) film layer with a compressible layer disposed thereon, is wrapped around an extremity with the film layer disposed against the skin. A tourniquet is placed onto the compressible layer, and wrapped about the extremity. The distal extension portion of the film layer is folded onto the tourniquet and secured in place. The contact of the non-slip film layer with the skin maintains the tourniquet padding and overlying tourniquet in place on the skin during a procedure.

In yet another aspect, the invention provides a cover sheet useful in making a tourniquet padding as provided according to the invention. The cover sheet is preferably made of a conformable material having at least one surface that has non-skid properties that can be provided, for example, by adhesive elements disposed on the surface, or by the properties of the conformable material itself. The cover sheet can optionally include perforations to separate the distal edge into sections or flaps. The width of the sheet is desirably wider than a tourniquet such that at least a portion of the sheet along the distal edge may be folded onto the tourniquet when positioned on the cover sheet. The cover sheet can comprise a variety of conformable materials, including, for example, a scrim reinforced material having fibers or filaments that are preferably at least partially embedded in the material and interwoven in a grid pattern in an open mesh web. Optionally, the sheet can be gathered along the distal and/or proximal edge portions, and further include an elastic element extending along the edge.

In another embodiment of a cover sheet, the sheet can comprise an elongate sheet of conformable material such as a scrim reinforced material, that is folded into two or more layers, for example, two cover sheets and one or more inner layers. Each of the cover sheets can include an adhesive element on the outer surface along a distal edge. One cover sheet can include one or more adhesive areas on the proximal outer surface. Another cover sheet can include perforations to separate the distal edge into sections.

In another embodiment of a cover sheet, the sheet comprises a single- or multi-layer stretch cling polymeric film, optionally with perforations along a distal edge to separate the edge portion into sections or flaps, and/or adhesive elements applied to a surface of the sheet to enhance attachment of the cover sheet to a surface, e.g., skin.

In another aspect, the invention provides a kit comprising the tourniquet padding contained in packaging, optionally with other items such as an adhesive element for securing the edge portions together, an adhesive element having a length sufficient to be wrapped around an extremity of a person, a tourniquet, instructions for its use with a tourniquet, and non-latex gloves, for example.

BRIEF DESCRIPTION OF THE DRAWINGS

Preferred embodiments of the invention are described below with reference to the following accompanying drawings, which are for illustrative purposes only. Throughout the following views, the reference numerals will be used in the drawings, and the same reference numerals will be used throughout the several views and in the description to indicate the same or like parts.

FIGS. 15A-15B are front perspective views of another embodiment of a tourniquet padding of the invention having a gathered proximal edge, with FIG. 15B showing the proximal edge of the padding extended.

FIGS. 16A-16B are rear perspective views of the tourniquet padding of FIGS. 15A-15B, with FIG. 16B showing the proximal edge of the padding extended.

FIG. 20 is a side view of the tourniquet padding of FIG. 18.

FIGS. 21A-21B are front views of embodiments of the tourniquet padding of FIG. 18 with a tourniquet positioned thereon.

FIGS. 22A-22B are side views of the tourniquet padding and tourniquet of FIGS. 21A-21B respectively taken along line 22A-22A, 22B-22B.

DETAILED DESCRIPTION OF THE PREFERRED EMBODIMENTS

Figure 1:
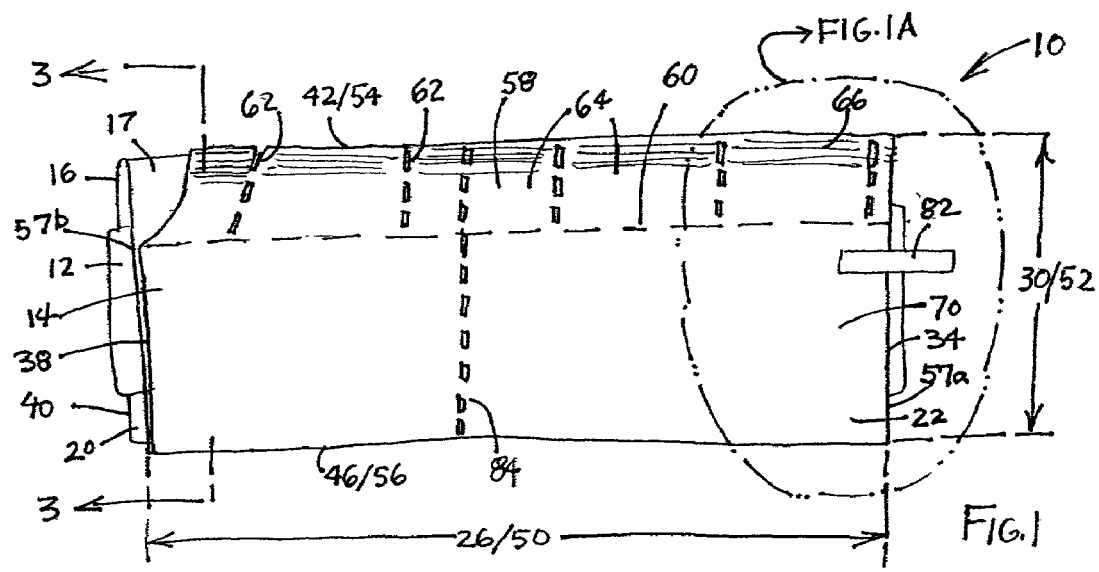
FIG. 1 is a front perspective view of an embodiment of a tourniquet padding of the invention.

The present invention encompasses a tourniquet padding for use with a tourniquet, and methods for making and using the tourniquet padding.

As used herein, the term "upper extremity" refers to the "arm" of a person including the shoulder, arm, elbow, forearm, wrist and hand. The term "lower extremity" refers to the "leg" of the person including the hip, thigh, knee, calf, ankle and foot.

A first embodiment of a tourniquet padding 10 of the present invention is described with reference to FIGS. 1-5. As shown, the tourniquet padding 10 comprises a padding material 12 disposed between a first (outer) cover sheet 14 and a second (inner) cover sheet 16. As depicted, the cover sheets 14, 16 are formed from a unitary sheet that is folded into at least three overlying layers to form the two cover sheets and one or more inner sheets 17. The padding layer 12 is positioned between the second cover sheet 16 and the inner sheet and provides a cushioning effect. In any of the embodiments described herein, the cover sheets and inner sheets can also comprise separate, individual sheets (not shown) placed on opposite sides of the pad. In addition, the padding layer 12 can be omitted, and the tourniquet padding can be used as an underlayer beneath a tourniquet to maintain the tourniquet in place and prevent it from slipping down the extremity, and/or as a covering to keep the tourniquet clean.

Each of the cover sheets 14, 16, has an inner surface 18, 20, an outer surface 22, 24, a length 26, 28, a width 30, 32, a first side edge 34, 36, a second side edge 38, 40, a distal edge 42, 44, and a proximal edge 46, 48. In use, as further discussed below, the tourniquet padding 10 is typically wrapped around a limb such that the second (inner) cover sheet 16 is applied against the skin 49 (FIGS. 5A-5B), and the distal edge 54 of the padding is oriented in the direction of the distal portion of the limb, i.e., the hand or foot. The proximal edge 56 of the tourniquet padding 10 is then oriented toward the proximal end of the limb, i.e., the shoulder or groin.

Referring to FIG. 1, the distal portion 58 of the first (outer) cover sheet 14 is foldable along a fold line 60 at its distal edge 42. The first cover sheet 14 can include scoring or indicia such as lining or arrows running longitudinally to indicate the fold line 60 (and where the inferior or distal edge of the tourniquet would be placed).

Figure 1A:
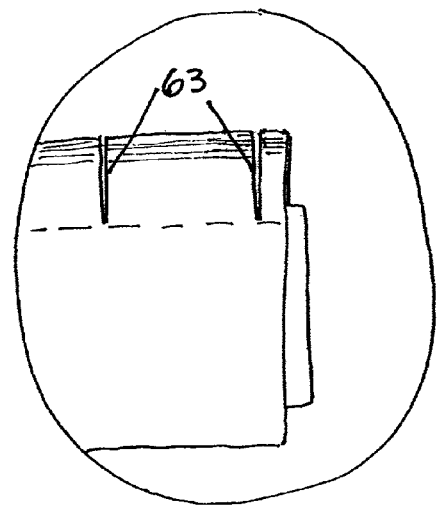
FIG. 1A is a fragmentary view of the tourniquet padding of FIG. 1 showing the incorporation of slits in the cover sheet.
Figure 4:
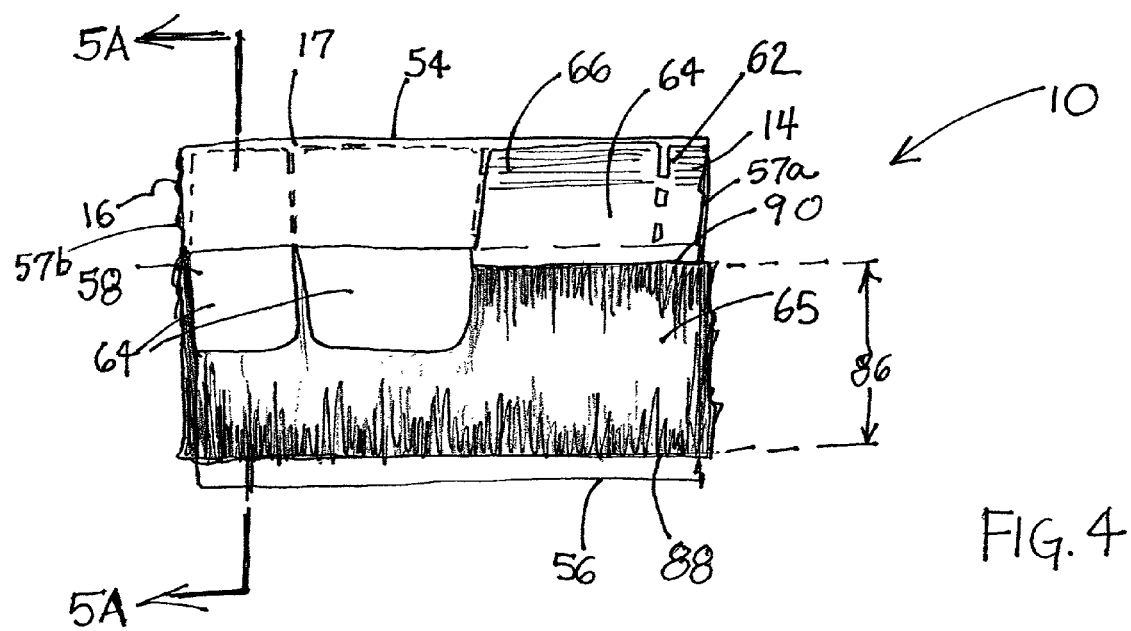
FIG. 4 is a front perspective view of the tourniquet padding of FIG. 1 with a tourniquet positioned thereon.
Figure 5A:
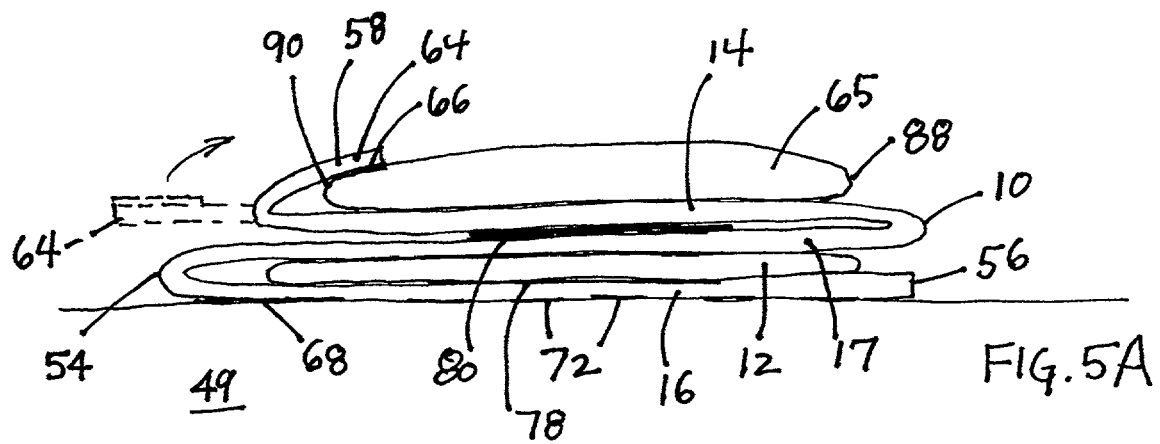
FIG. 5A is a side view of the tourniquet padding and tourniquet of FIG. 4, taken along lines 5A-5A showing placement of a portion of the tourniquet padding onto the tourniquet.
Figure 5B:
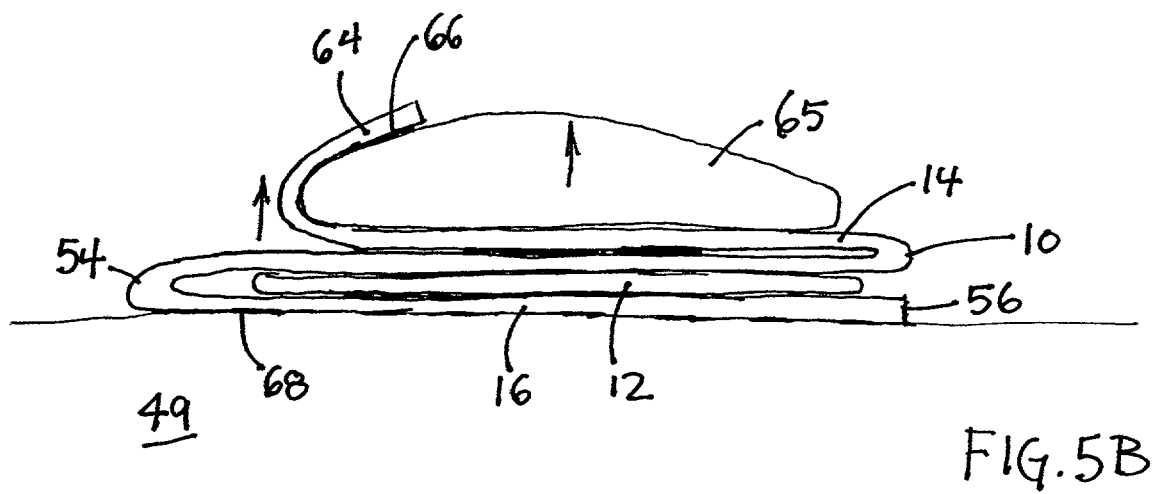
FIG. 5B is a side view of the tourniquet padding and tourniquet of FIG. 5A, showing the tourniquet inflated during use.

It is also desirable that the first cover sheet 14 includes perforations 62, or slits 63 as shown in FIG. 1A, that are spaced apart at regular intervals along the length 26 of the distal edge 42, for separating the distal edge into sections or flaps 64. In use, as shown in FIG. 4, the distal portion 58 of the cover sheet 14 is turned proximally over a tourniquet 65 positioned on the cover sheet 14 near the fold line 60. The perforations 62 or slits 63 allow the cover sheet 14 to separate and accommodate the changing size (i.e., thickness) of the tourniquet 65 as it inflates and deflates. As depicted in FIGS. 5A-5B, the distal portion 58 of the first (outer) cover sheet 14 lifts upward as the tourniquet inflates while the second (inner) cover sheet 16 remains secure to the skin 49. This arrangement advantageously avoids pulling on the second cover sheet 16 and the underlying skin 49 so that there is little or no blistering of the skin as the tourniquet is inflated and deflated.

Figure 2:
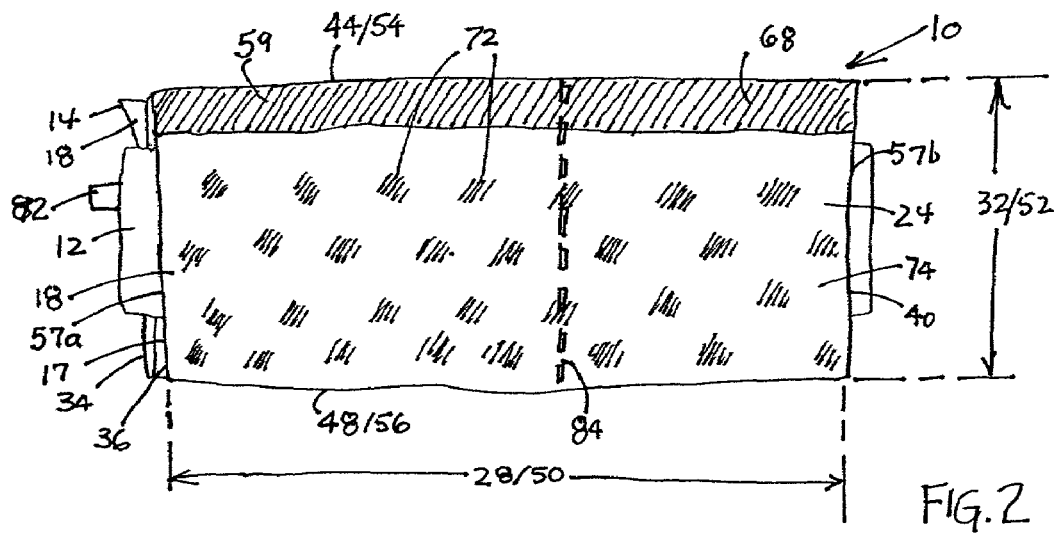
FIG. 2 is a rear perspective view of the tourniquet padding of FIG. 1.
Figure 3:
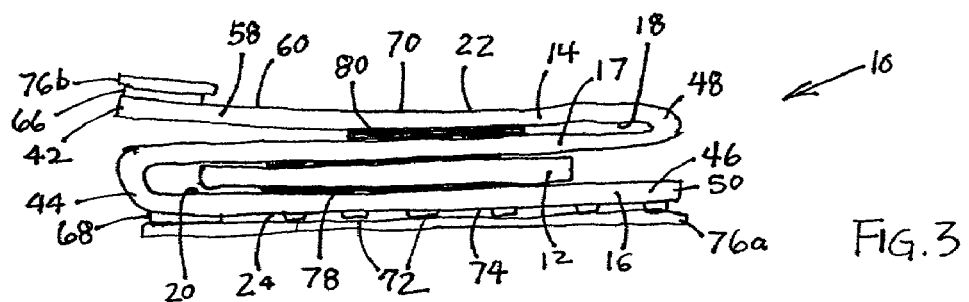
FIG. 3 is a side view of the tourniquet padding of FIG. 1, taken along lines 3-3.

Referring to FIGS. 1-3, adhesive material is applied along the distal edges 42, 44 of the outer surfaces 22, 24 of the cover sheets 14, 16. The adhesive is applied as a strip or band 66, 68, along the length 26, 28 of the cover sheets, and can be in the form of a solid band, intermittent lines, dots or other discrete or disconnected segments, and the like. The strip of adhesive 66 along the edge 42 of the first cover sheet 14 is typically about 0.5 to about 1 inch wide, and sufficient to securely adhere the distal portion 58 of the first cover sheet 14 on the surface of a tourniquet 65 and maintain the tourniquet in position on the padding 10 during use. Although not shown, the proximal surface area 70 of the first (outer) cover sheet 14 can further comprise a solid layer or lines or other discrete areas of adhesive to hold the tourniquet in place on the cover sheet 14 during use.

As depicted in FIG. 2, the second (inner) cover sheet 16 includes a strip of adhesive 68 along the distal edge 44, and one or more discrete areas 72 of adhesive such as oblique/vertical strips and/or spots or spaced apart areas arranged over its proximal surface area 74. The strip of adhesive strip 68 and the adhesive areas 72 are sufficient to adhere the tourniquet padding 10 to the skin 49, and inhibit the padding and tourniquet from slipping along a limb during use. The strip of adhesive 68 is typically about 0.5 to about 1 inch wide. It is preferred that adhesive is not applied as a solid layer over the proximal surface area 72 of the second cover sheet 16 because, as the tourniquet is inflated, it would pinch the skin as the circumference of the extremity is decreased in size by compression of the tourniquet. The strip of adhesive 68 along the distal edge 44 of the cover sheet can comprise a solid band of adhesive because that section of the tourniquet padding is not compressed during inflation of the tourniquet.

The adhesive material that is used in conjunction with the tourniquet padding, particularly on the second (inner) cover sheet 14 that is placed against the skin, is preferably a biocompatible and hypoallergenic adhesive material that is adherable to skin but will release from the skin with minimal trauma. Such adhesives are well known in the art and commercially available. Useful adhesives include, for example, acrylic adhesives that are used in surgical applications where reduced skin trauma is required. Preferably, the adhesive is a pressure-sensitive adhesive substance.

In another embodiment, the adhesive strip 68 and adhesive areas 72 comprise a frictionally adhesive material having anti-slip properties, as, for example, latex rubber, silicon rubber, or foamed polyvinyl chloride, with a typical thickness of about 0.001 to about 0.5 mm. Such materials are described for example, in connection with anti-slip socks used in hospitals, hotels, and the like, non-slip garments, and non-slip mats, such as in U.S. Pat. No. 6,332,825 (Henrickson), U.S. Pat. No. 6,041,443 (Pas et al.), U.S. Pat. No. 6,022,617 (Calkins), and U.S. Pat. No. 5,901,706 (Griesbach et al.), the disclosures of which are incorporated by reference herein. The anti-slip material can be applied as a coating to the surface 74 of the cover sheet 16 in a dot, grid, or suitably designed pattern, to effect suitable surface resistance of the cover sheet 16 on the skin. Suitable coating methods for applying the anti-slip material include, for example, solution coating, gravure coating, and print coating, among others. The anti-slip material can be pigmented if desired. The anti-slip material provides frictional adhesion to reduce slippage of the tourniquet padding during use.

As shown in FIG. 3, it is also desirable that the adhesive surfaces are protected by a suitable removable covering or releasably attached release or slip sheet 76a-b. For example, a release sheet 76a can be applied as a cover over the entire surface of the cover sheet, as a longitudinal strip 76b over the adhesive band 66 along the edge 42 of the cover sheet 14, or a panel section (not shown) over the proximal surface areas 70, 74 of the cover sheets, and combinations thereof. The release sheets 76a, 76b can then be peeled off just prior to applying the tourniquet padding to the limb. In an embodiment in which the first cover sheet 14 includes slits 63, as depicted in FIG. 1A, an overlying peel-off layer 76b placed over the adhesive 66 can serve to maintain the sections 64 in place before being applied to the tourniquet.

The cover sheets 14, 16 provide a flexible yet strong covering over the inner padding 12, and can be manufactured from any suitably compliant, natural or synthetic (man-made) material including but not limited to, paper, scrim reinforced tissue or other reinforced scrim material, crepe, cloth, terry cloth, cheesecloth, plastic (polymer film), and the like, and combinations thereof. Also useful are non-woven fabrics such as felt (carded non-woven) made from polyester, rayon or other fiber, or absorbent web (airlaid non-woven) made from wood pulp or synthetic fibers typically used for diapers, baby wipes, sanitary towels, drapes and gowns, among other products. The cover sheet can be fabricated as a laminate, for example, a laminate of tissue and a non-woven or woven substrate, a laminate of a polymer film (e.g., polyethylene) backing and non-woven or woven substrate material such as a tissue/poly laminate similar to that used for dental bibs and table coverings, a polyurethane foam-polymer film laminate (thermo- or adhesively laminated) similar to that used for EMS blankets, and the like. Preferably, the cover sheets are composed of a material that is porous (breathable) to pass moisture, vapor and air.

A preferred material comprises a lightweight conformable scrim reinforced material that allows the tourniquet padding to readily flex and bend about the extremity. Scrim reinforced materials are well known and widely used, and comprise threads or filaments. Preferably, the scrim fibers or strands are embedded or partially embedded in the material, and are preferably interwoven at about right angles in an open mesh web or grid. Suitable scrims can be made from paper, knits, wovens, non-wovens and extruded porous sheets such as materials available from Conweb, Minneapolis, Minn. Examples of suitable scrim filaments include fiberglass and ceramic fibers, and fibers made of polyester, polyethylene and other polyolefins, polyacrylate, rayon, cotton, hemp, jute, natural rubber, polyurethane, and blends thereof. Scrim materials are also described, for example, in U.S. Pat. Nos. 6,027,465, 6,100,206, and 6,132,835 (Scholz et al., 3-M Company), the disclosures of which are herein incorporated by reference.

The padding layer 12 provides a cushioning sufficient to prevent the skin of a person from being pinched by a tourniquet 65 mounted on the tourniquet padding 10 and wrapped around a limb of the person. Typically, as shown, no padding is provided in the distal portions 58, 59 of the cover sheets 14, 16. The padding 12 can comprise a porous or non-porous material, or a natural or synthetic fiber material. A desirable padding material is cast padding, which can be made from cotton, nylon, rayon, acrylic, polyester, and other like materials and blends. Other suitable materials include a paper material, a scrim reinforced material, a foamed material such as a polyurethane foam, or other material having memory that will return to its pre-compressed shape after being compressed, and combinations thereof.

Preferably, the materials used in making the tourniquet padding are sterilizable. As such, the tourniquet padding can be sterilized and packaged to provide a clean surface along the edge of a surgical field adjacent the tourniquet.

In assembling the cover sheets 14, 16 and the padding layer 12, it is desirable to bond the padding layer to at least the second cover sheet 16, as depicted by the adhesive area 78 in FIG. 3. The padding can be attached to the cover sheet(s), for example, with an adhesive, by stitching and/or by thermal bonding. Optionally, but preferably, at least a portion of the inner surface of the first (upper) cover sheet (proximal to the fold line) is bonded to the inner layer, for example by adhesive areas 80, as shown in FIG. 3. Adhesive is then applied onto the outer surfaces of each cover sheet along the distal edge and onto one or more areas of on the outer surface of the second cover sheet, and a cover sheet is applied over the adhesive areas.

The tourniquet padding 10 can optionally include a member 82 such as an adhesive tab attached at either or both of the side edges 14, 16 for securing the end of the tourniquet padding 10 together around the limb.

The length 50 of the tourniquet padding 10 is sufficient to allow the padding to be wrapped around the limb, with the side edges 34/36, 38/40 of the cover sheets 14, 16 meeting up or overlapping. Since the length 50 that is needed will vary according to the application, it is desirable to provide the tourniquet padding in rolls. Typically, for an adult, the tourniquet padding 10 ranges between approximately 8 inches to approximately 26 inches in length. The padding 10 can be cut from the roll to a desired length, or can include perforations 84 at intermittent locations along the length, as shown in FIGS. 1-2, which extend through the cover sheets 14, 16 and padding 12 to allow the tourniquet padding 10 to be separated into sections.

Tourniquets vary in width and are generally available in widths of 2, 4 or 6 inches. Dual bladder ("Bier blocks") and other specialized tourniquets can be, for example, 8 to 9 inches in width. In the use of a Bier block tourniquet, the proximal bladder is inflated, a local anesthetic is injected into a vein, and the arm is elevated to cause the anesthetic to migrate proximally to the edge of the proximal tourniquet, which produces numbness in the extremity. The second tourniquet is inflated over an anesthetic area of the arm, and the proximal tourniquet is deflated. This arrangement substantially eliminates tourniquet pain.

The width 52 of the tourniquet padding 10 can be varied to accommodate the width 86 of the tourniquet 65. In general, the width 52 of the tourniquet padding is sufficient to receive a tourniquet thereon such that there is no or a minimal amount of contact of the tourniquet with the skin in order to minimize pinching of the skin during the inflation/deflation of the tourniquet, and/or trauma to the skin from contact of the proximal edge of the tourniquet.

Referring to FIGS. 4 and 5A-5B, in use, a tourniquet 65 is positioned on the tourniquet padding 10 such that the distal portion 58 of the first (outer) cover sheet 14 may be folded over at least a portion of the tourniquet. Preferably, the tourniquet padding 10 is wider than the tourniquet such that when the first cover sheet 14 is folded onto the tourniquet, the proximal edge 56 of the tourniquet padding extends beyond the proximal edge 88 of the tourniquet. For example, in the use of a tourniquet 65 that is about 4 inches wide, the tourniquet padding is preferably at least about 5½ inches wide so that, in positioning the tourniquet on the padding, at least about ½-inch of the tourniquet padding extends beyond the proximal edge 88 of the tourniquet, and at least about 1-inch of the tourniquet padding extends beyond the distal edge 90 of the tourniquet. In addition, either cover sheet can be as wide or wider than the other cover sheet.

Figure 6:
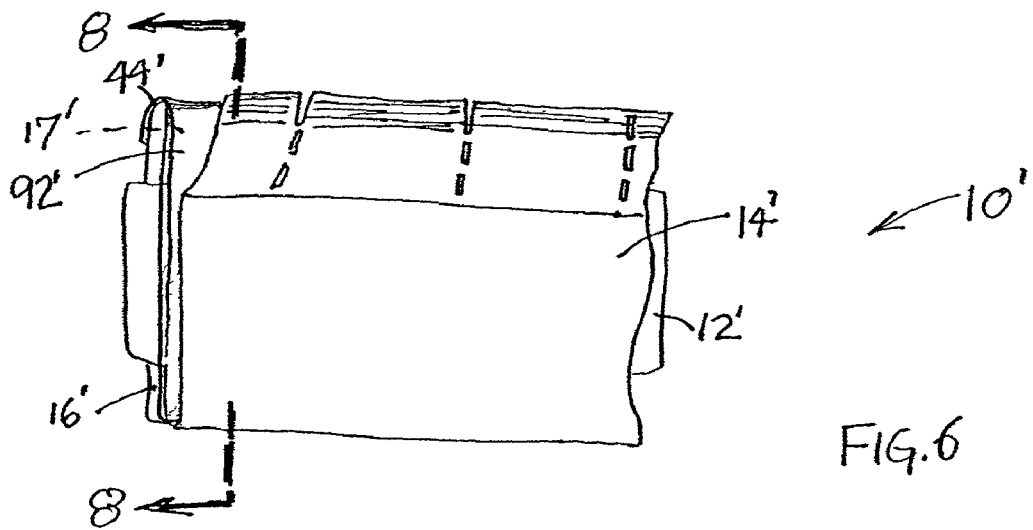
FIG. 6 is a front perspective view of another embodiment of a tourniquet padding of the invention that includes a liquid-impermeable layer.
Figure 7:
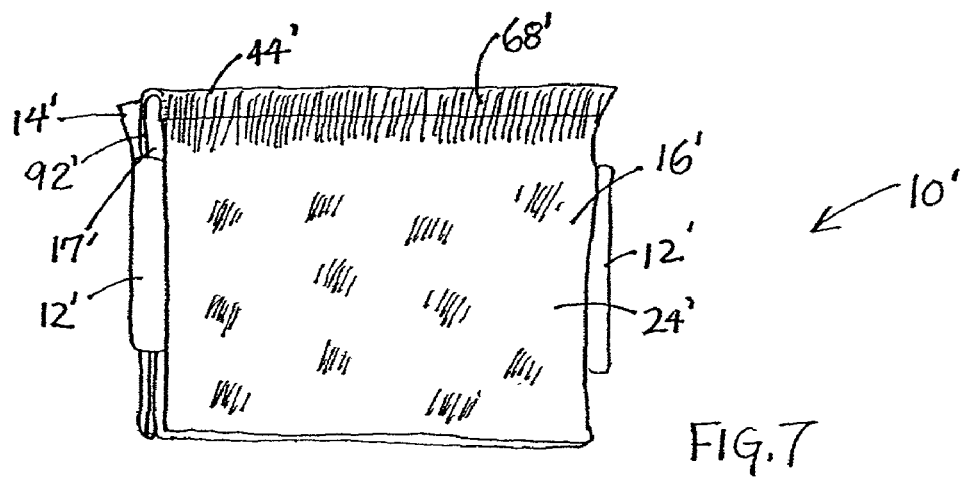
FIG. 7 is a rear perspective view of the tourniquet padding of FIG. 6.
Figure 8:
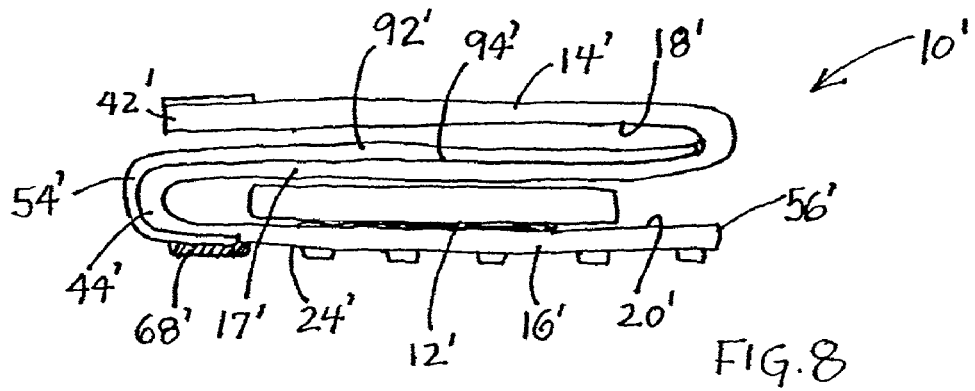
FIG. 8 is a side view of the tourniquet padding of FIG. 6, taken along lines 8-8.

Referring now to FIGS. 6-8, in another embodiment of a tourniquet padding 10' according to the invention, the surfaces directed "down" the extremity (distally) are made to be waterproof, so that the prepping and other solutions used in surgery are not absorbed and/or wicked into the tourniquet padding positioned underneath the tourniquet. As depicted, a layer 92' of a liquid-repellent material has been bonded to the surface 94' of the inner sheet 17' and extends over the distal edge 44' and onto at least a portion of the outer surface 24' of the second (inner) cover sheet 16'. Suitable liquid-repellent materials include those that repel and/or are impermeable or impervious to liquids, including, for example, polyethylene or other plastic sheeting material. As shown in FIG. 8, the adhesive layer 68' along the distal edge 44' on the outer surface 24' of the second cover sheet 16' is then applied onto the plastic sheeting 92'.

Figure 9:
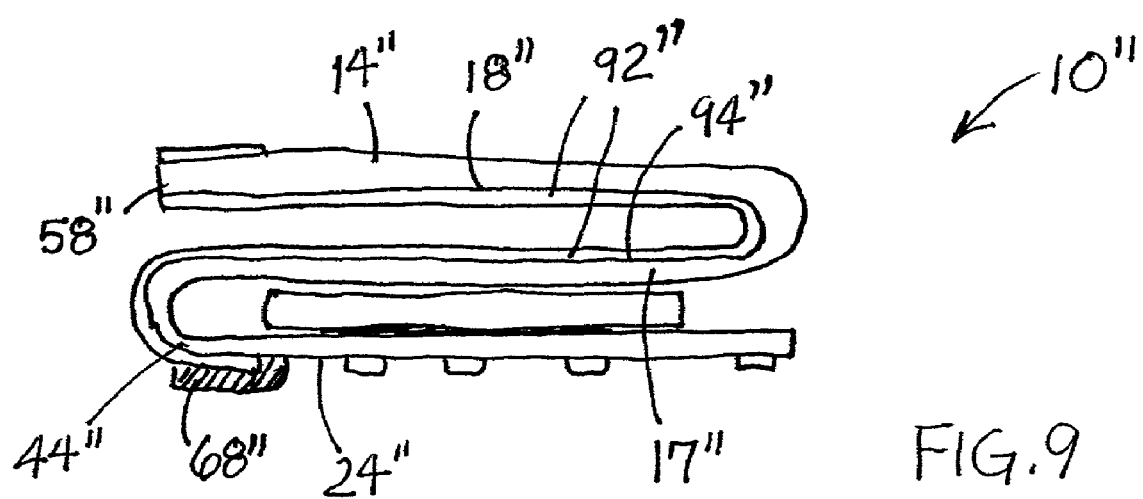
FIG. 9 is a side view of another embodiment of the tourniquet padding of FIG. 6, taken along lines 8-8, showing an extension of the liquid-impermeable layer.

The portion of the first (upper) cover sheet applied to the tourniquet helps protects at least the distal edge of the tourniquet from extraneous liquids and other materials that can soil the tourniquet. To that end, as depicted in FIG. 9, it is preferred that the liquid-repellent layer 92" is applied to the first inner surface 18" of the first cover sheet 14". When the distal portion 58" of the first cover sheet 14" is adhered onto the tourniquet, the plastic sheeting 92" will provide a protective covering for at least the distal edge of the tourniquet. More complete coverage of the surface of the tourniquet can be achieved by widening the first cover sheet 14" and attaching the distal portion 58" at or near the proximal edge of the tourniquet.

Although not shown, a liquid-repellent layer can be bonded only to the cover sheet, for example, the inner surface (18') of the first (upper) cover sheet and/or the inner surface (20') of the second (inner) cover sheet, and not over the distal edges (42', 44') to make only the surfaces of the cover sheets waterproof.

Figure 10:
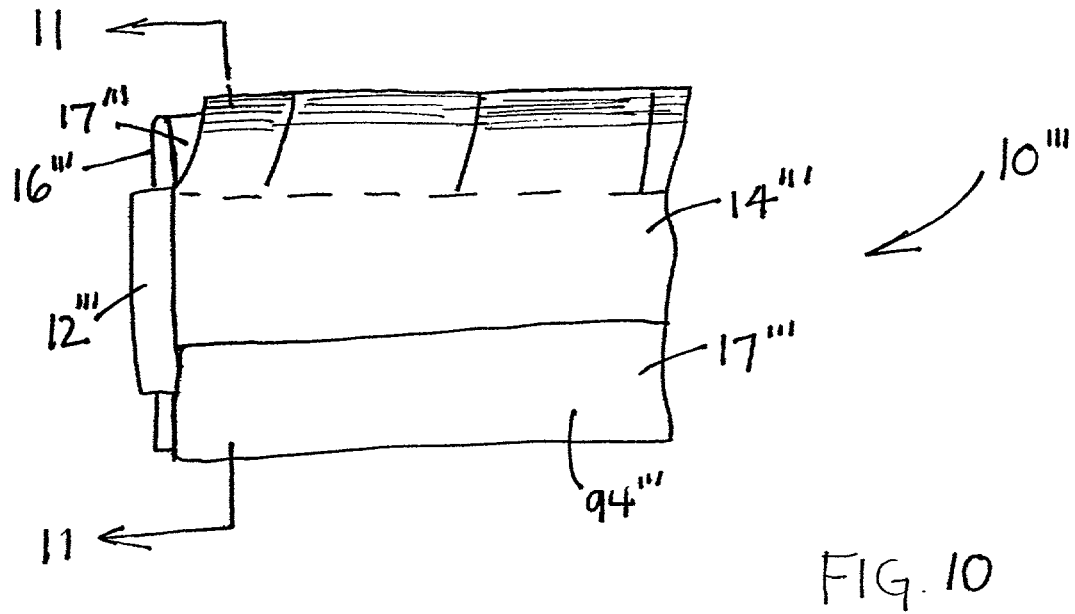
FIG. 10 is a front perspective view of another embodiment of a tourniquet padding of the invention showing the cover sheet attached to an inner sheet layer.
Figure 11:
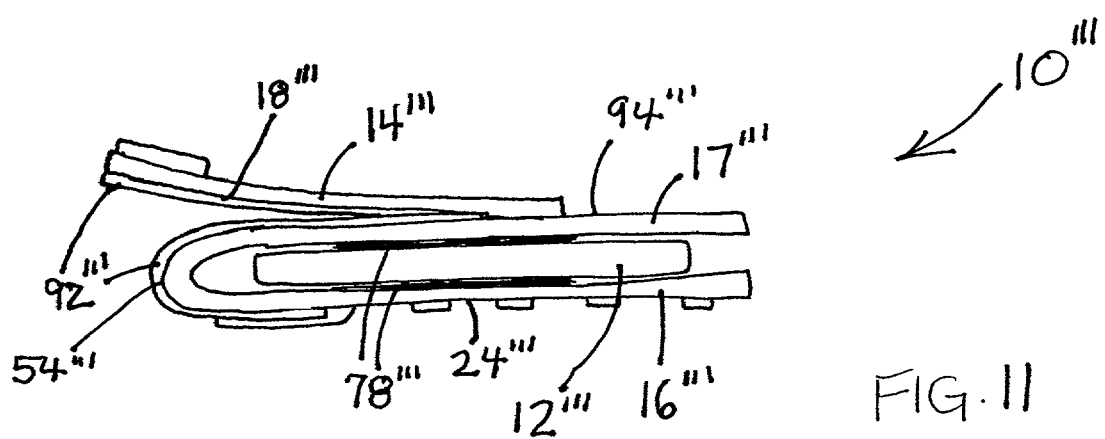
FIG. 11 is a side view of the tourniquet padding of FIG. 6, taken along lines 11-11.

Another embodiment of a tourniquet padding 10''' according to the invention is shown in FIGS. 10-11. The tourniquet padding comprises a unitary sheet that is folded into at least two layers to form the second (inner) cover sheet 16''' and at least one overlying (inner) layer 17'''. A padding material 12''' is disposed between and attached by adhesive areas 78'' to the inner layer 17''' and the second cover sheet 16'''. The first (outer) cover sheet 14''' is attached to the surface 94''' of the inner layer 17'''. As also shown, a liquid-impermeable sheet 92''' is affixed to the inner surface 18''' of the first cover sheet 14''' to protect the surface of the tourniquet during a procedure. A liquid-impermeable sheet 92''' is also shown affixed to the surface 94''' of the inner layer 17''', and extends over the distal edge 54''' of the tourniquet padding and onto the outer surface 24''' of the second cover sheet to protect the padding material 12''' from becoming wet.

Figure 12:
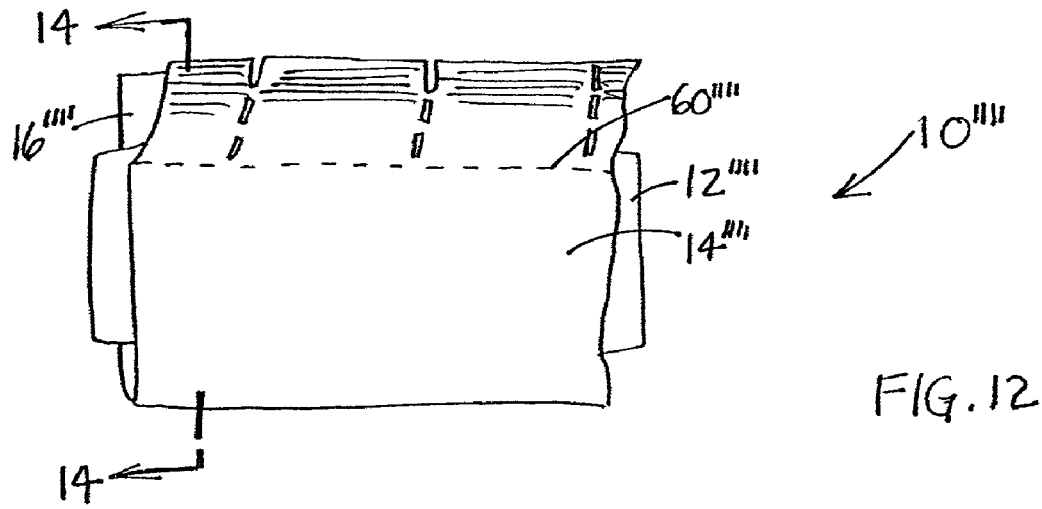
FIG. 12 is a front perspective view of another embodiment of a tourniquet padding of the invention.
Figure 13:
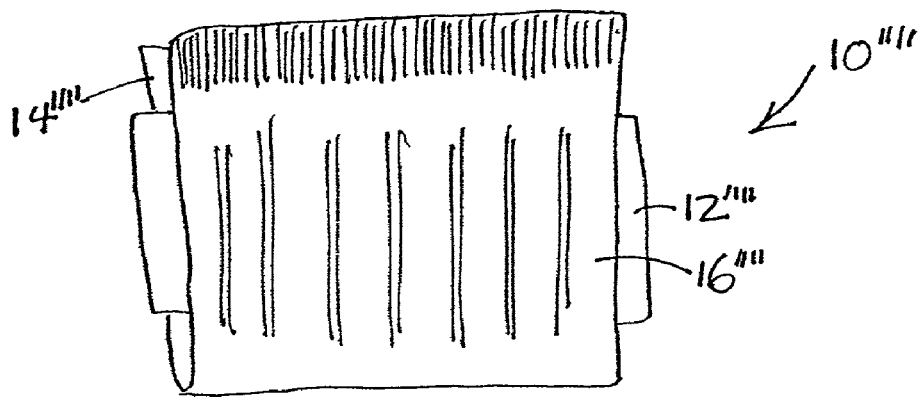
FIG. 13 is a rear perspective view of the tourniquet padding of FIG. 12.
Figure 14:
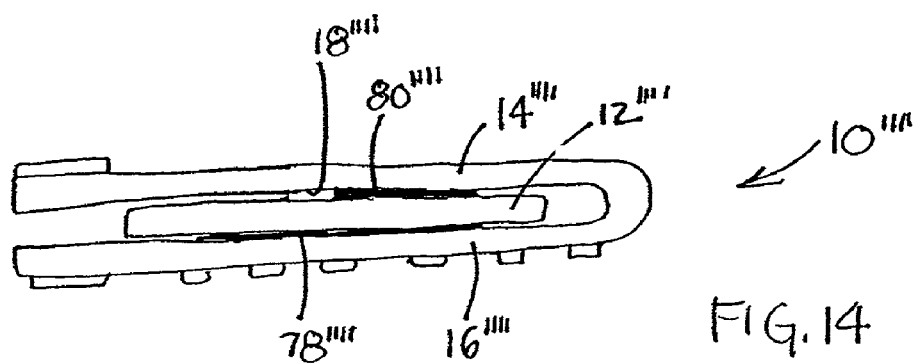
FIG. 14 is a side view of the tourniquet padding of FIG. 12, taken along lines 14-14.

Yet another embodiment of a tourniquet padding 10'''' according to the invention is shown in FIGS. 12-14. As depicted, the cover sheets 14'''', 16'''' are shown as a unitary sheet that is folded in about half with the padding material 12'''' sandwiched therebetween. The padding layer 12'''' is positioned between and affixed to the second (lower) cover layer 16'''', for example by an adhesive bonding 78''''. A portion of the inner surface 18'''' of the first (upper) cover sheet 14'''' (proximal to the fold line 60'''') is also shown as bonded to the padding layer 12'''' by adhesive area 80''''.

The tourniquet padding can also have an element of elasticity to accommodate its application to a range of sizes of extremities having varying circumferences. For example, in another embodiment, the cover sheets of the tourniquet padding may be gathered to make it slightly elastic in order to accommodate extremities (arm/leg) of varying diameter or circumference. As depicted in FIGS. 15A-16A, the cover sheets $14^v$, $16^v$ of the tourniquet padding $10^v$ are pleated or crimped (corrugated) along the proximal edge $56^v$. When the tourniquet padding is then wrapped around a limb of a person, the cover sheets may be spread/extended along the proximal edge, as shown by the arrows in FIGS. 15B-16B, to wrap around a portion of the limb having a wider circumference than at the distal edge $54^v$ of the tourniquet padding.

Figure 17A:
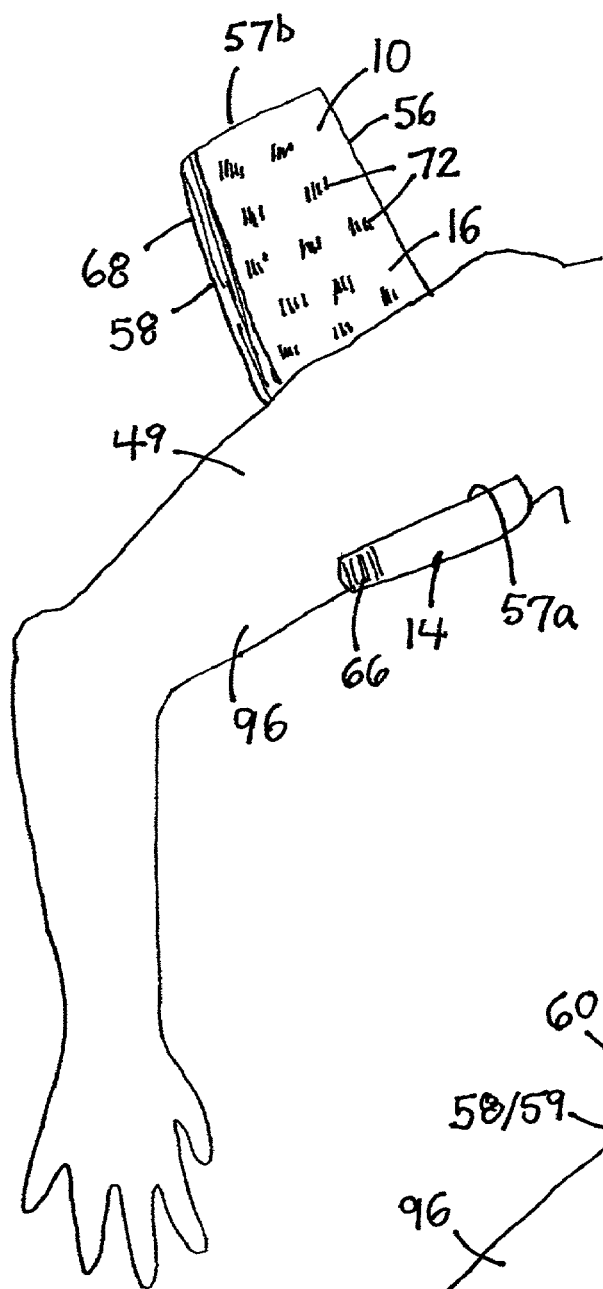
FIGS. 17A-17E are views of the tourniquet padding of FIG. 1 at sequential steps of applying the tourniquet padding and a tourniquet on the upper arm of a person.
Figure 17B:
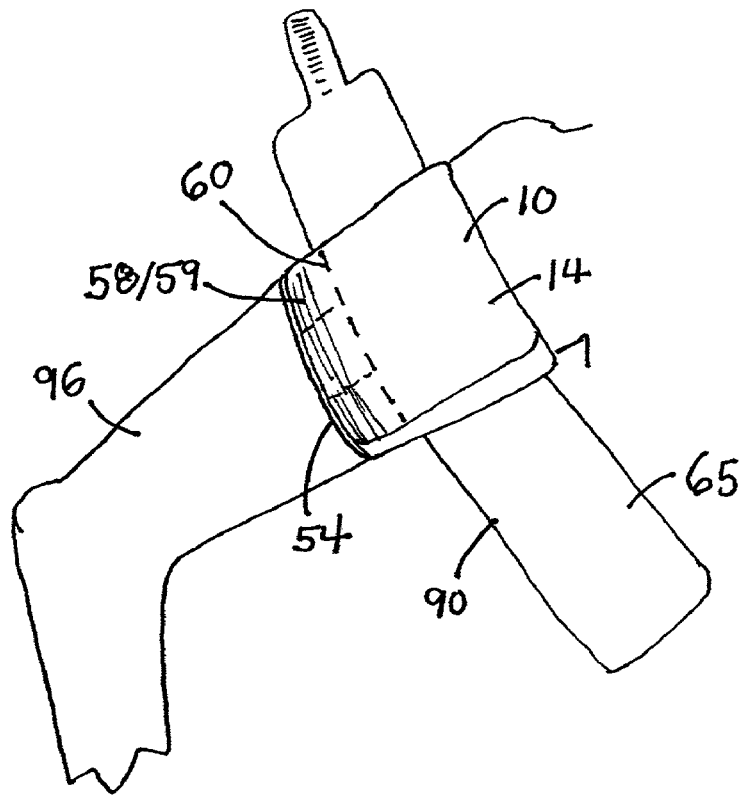
Figure 17C:
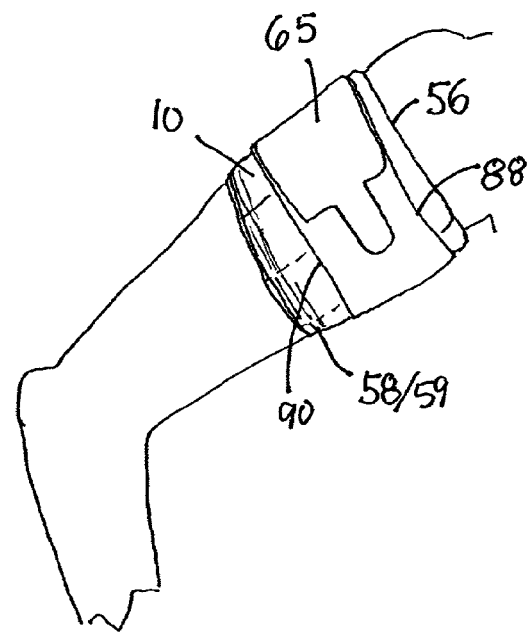

A use of the tourniquet padding 10 depicted in FIGS. 1-5 is shown in FIGS. 17A-17E. The releasable sheet 76a is first removed from the adhesive strip 68 and adhesive areas 72 on the second (inner) cover sheet 14. As shown in FIGS. 17A-17B, the tourniquet padding 10 is then wrapped around the limb 96 of the person, shown as the upper extremity, preferably with the ends 57a, 57b slightly overlapping, and the adhesive areas 68, 72 on the second cover sheet 16 are secured to the skin 49. A tourniquet 65 is then wrapped around the tourniquet padding 10 such that the distal edge 90 of the tourniquet is at or near the fold line 60 of the first cover sheet 14. As shown in FIG. 17C, the distal edge portions 58, 59 of the first and second cover sheets 14, 16 extend beyond the distal edge 90 of the tourniquet. The proximal edge 56 of the tourniquet padding also extends beyond the proximal edge 88 of the tourniquet.

Figure 17D:
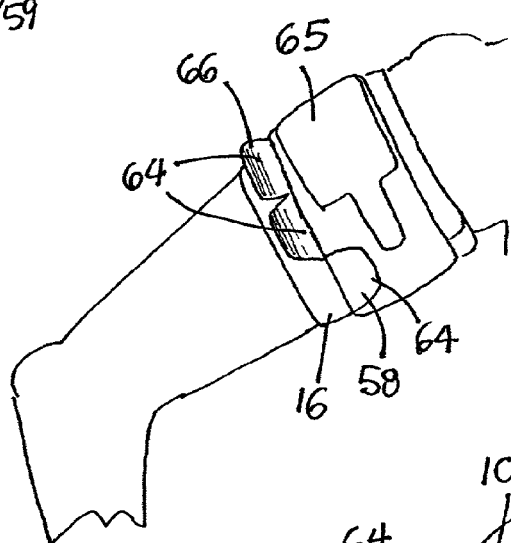
Figure 17E:
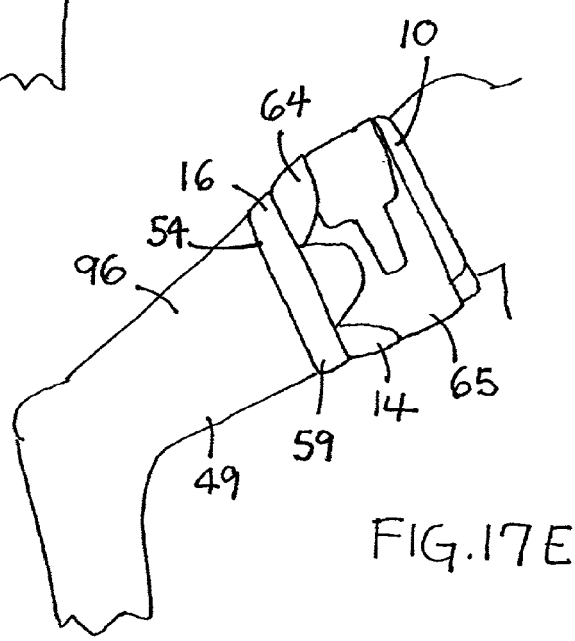
Figure 18:
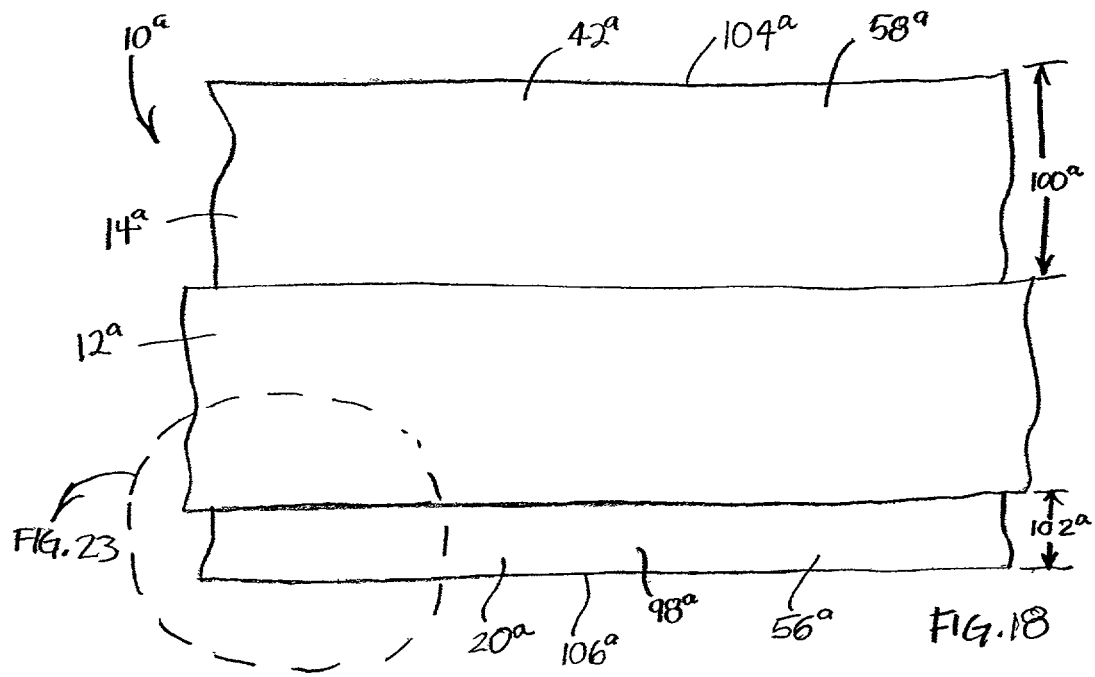
FIG. 18 is a front view of another embodiment of a tourniquet padding of the invention having a single cover sheet with an overlying padding material attached thereto.
Figure 19:
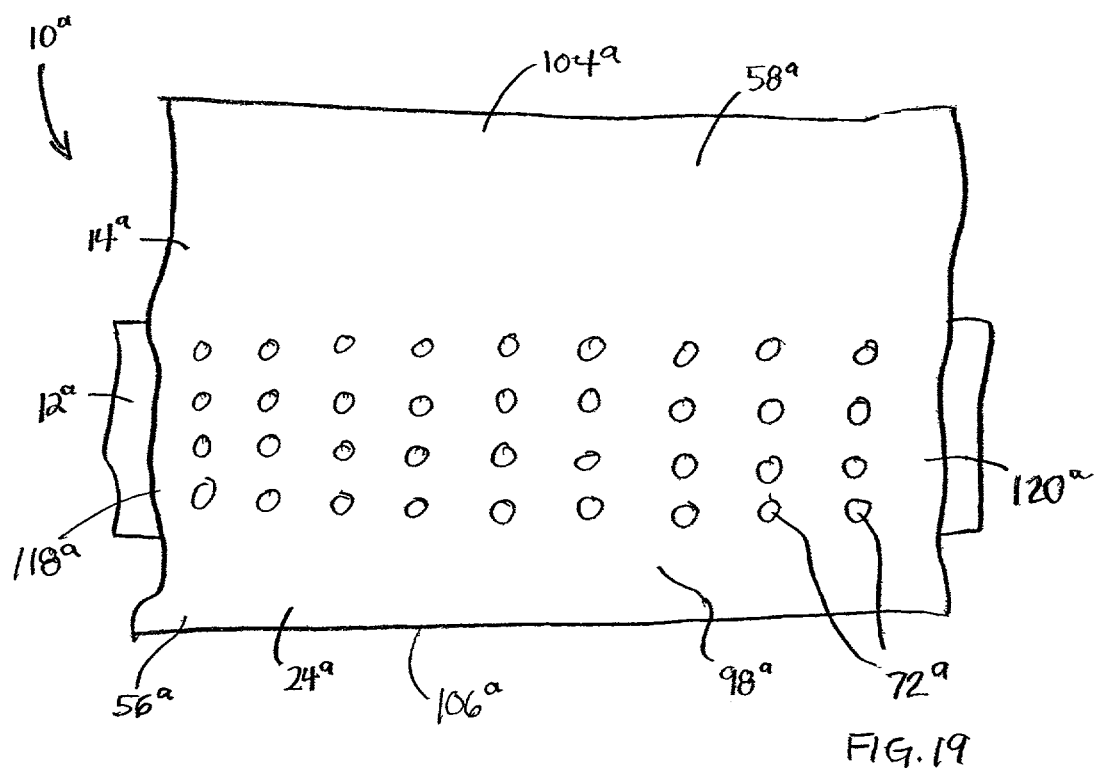
FIGS. 19, 19A are rear views of the tourniquet padding of FIGS. 18, 18A, respectively.
Figure 18A:
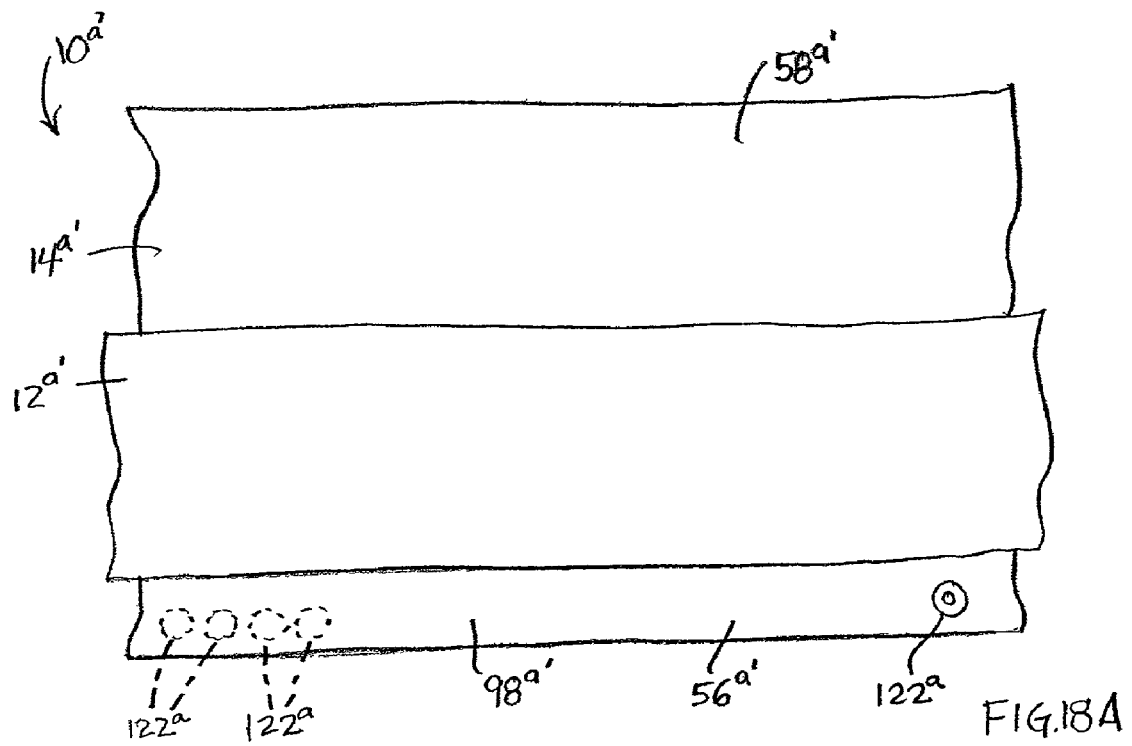
FIG. 18A is another embodiment of the tourniquet padding of FIG. 18, having fastening members (e.g., snaps) along the proximal edge portion.
Figure 19A:
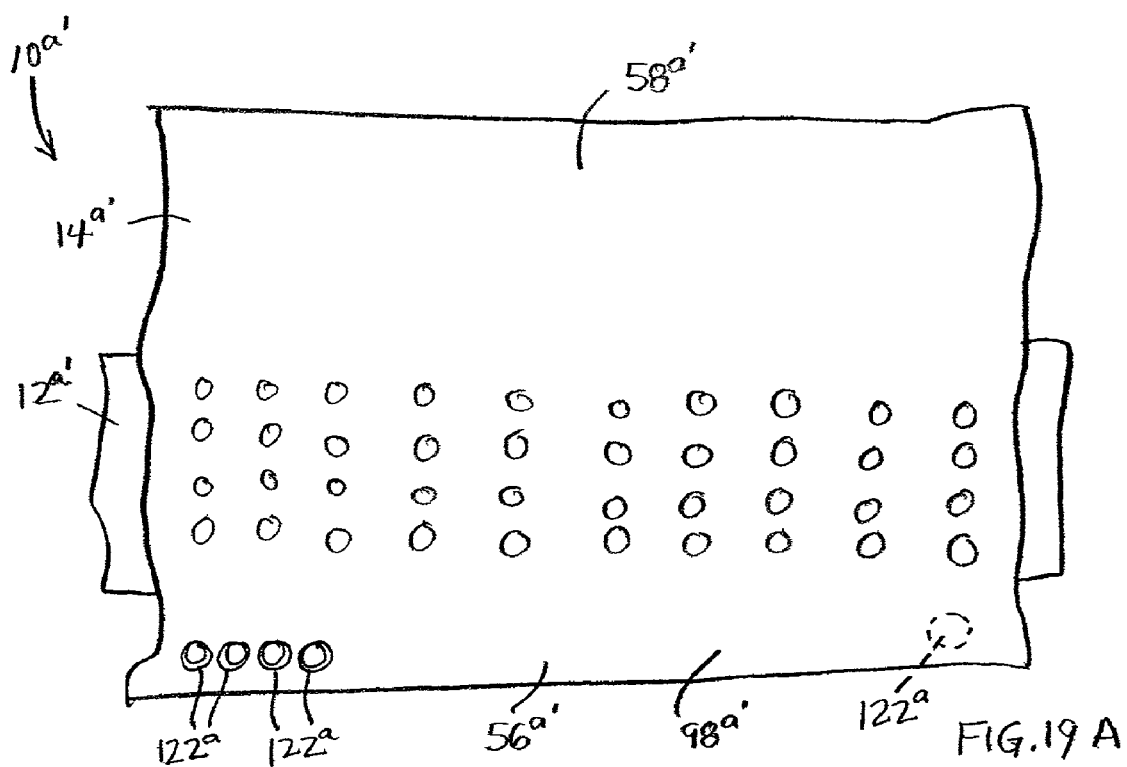

As depicted in FIG. 17D, the distal portion 58 of the first cover sheet 14 is then turned proximally over the lower or distal edge 90 of the tourniquet 65, and adhered to the tourniquet by means of the adhesive 66. This keeps the tourniquet from slipping down the arm/leg, protects it from fluids used for prepping the skin, and generally keeps the tourniquet clean. As depicted, the distal portion 58 has been separated into sections or flaps 64 by means of the perforated lines 62. As shown in FIG. 17E, the tourniquet 65 is thus securely positioned over the tourniquet padding 10 around the limb 96 of the user, and can be inflated and deflated with no or minimal slipping down the limb of the person.

In the use of the tourniquet padding depicted in FIGS. 6-9, the inclusion of a liquid-impermeable layer 92'' in the design of the device helps prevent liquids that may be applied to the limb from coming into contact with the padding. Referring to FIG. 17E, the adherence of the distal portion 59 of the second (inner) cover sheet 16 to the skin and the presence of a liquid-impermeable layer (not shown) over the distal edge 54 of the tourniquet padding substantially prevents liquid from contacting the portion of the padding underlying the tourniquet 65.

Another embodiment of a tourniquet padding $10^a$ is depicted in FIGS. 18-22. The tourniquet padding comprises a single cover sheet $14^a$ with a compressible material layer $12^a$ disposed thereon. The padding layer $12^a$ is positioned on the film coversheet $14^a$ such that a distal portion (flap) $58^a$ and a proximal portion (flap) $98^a$ are provided. Adhesive elements $72^a$ as described for tourniquet padding 10, can be optionally disposed on the skin-side surface of the cover sheet $14^a$. The width $100^a$ of the distal flap portion $58^a$ and/or the width $102^a$ of the proximal flap portion $98^a$ allows either or both flaps to be folded completely over the tourniquet $65^a$ positioned on the padding $12^a$ to cover the tourniquet as depicted, for example, in FIGS. 21A-B, 22A-B. As shown in FIGS. 21A/22A, the flap portions $58^a$, $98^a$ have been folded onto the tourniquet $65^a$ with the ends overlapping. Optionally, one or more adhesive elements $82^a$ such as adhesive paste, two-sided tape, or tab (as shown), can be used to secure the overlapping flaps $58^a$, $98^a$ of the cover sheet $14^a$. As another option, an adhesive element $82^a$ (e.g., adhesive paste, two-sided tape, etc.), can be used to secure the ends of the flaps $58^a$, $98^a$ together, as shown in FIGS. 21B/22B.

Figure 23A:
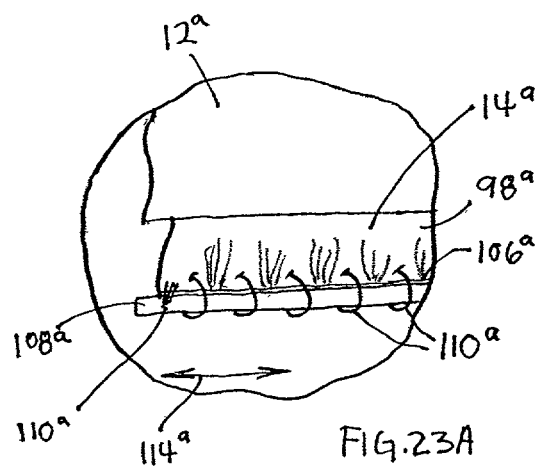
FIGS. 23A, 23B, 23C, 23D, 23E and 23F are partial front views of the tourniquet padding of FIG. 18 showing embodiments of an elastic element attached to the cover sheet.
Figure 23B:
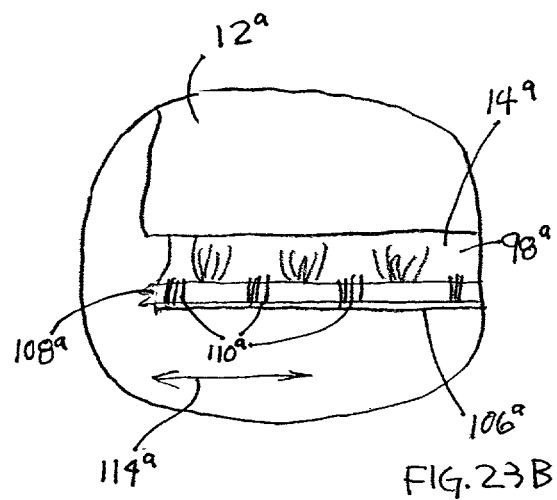
Figure 23C:
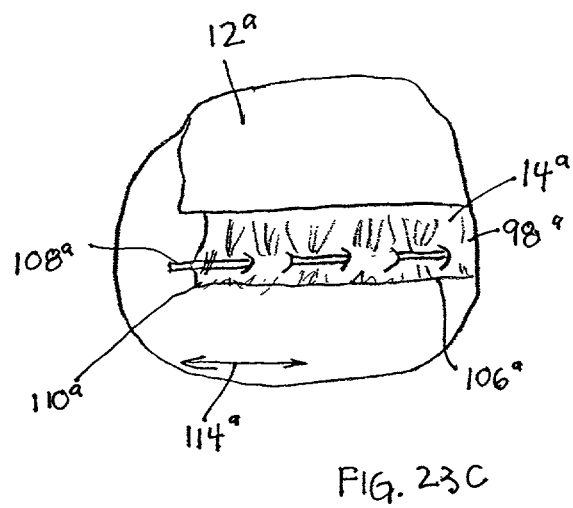
Figure 23D:
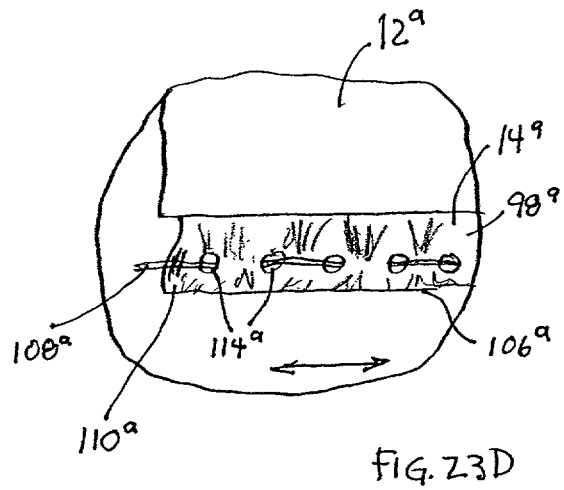
Figure 23E:
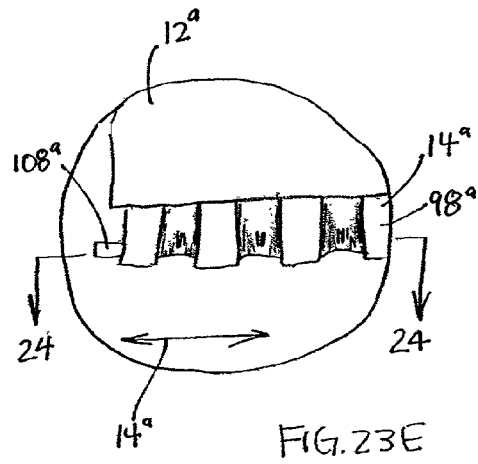
Figure 23F:
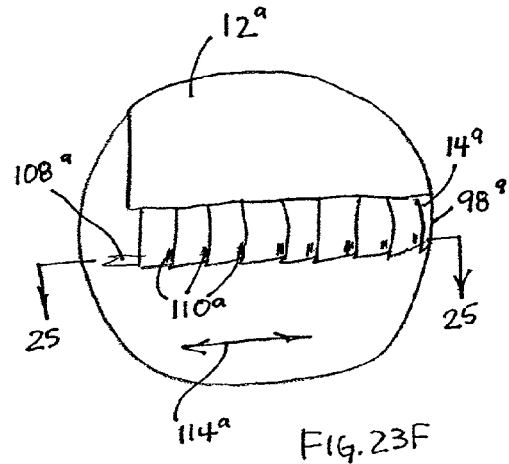
Figure 24:
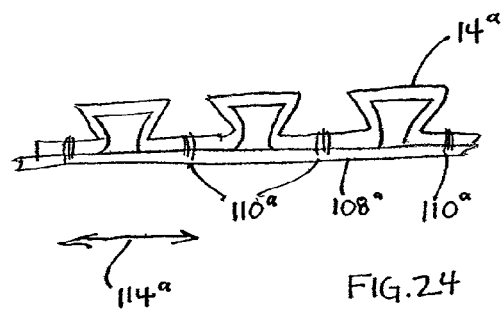
FIGS. 24 and 25 are end views of the cover sheets of FIGS. 23E and 23F taken respectively along line 24-24, 25-25.
Figure 25:
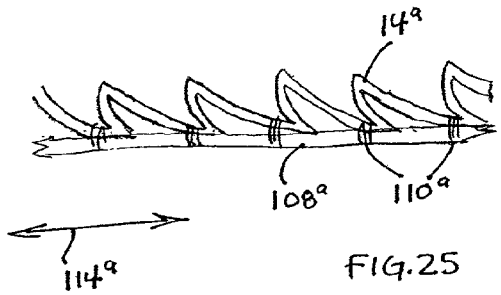

In addition to the embodiments shown in FIGS. 15-16, to add an element of elasticity to the cover sheet, the flap portions $58^a$ and/or $98^a$ can be pleated, crimped, corrugated, or otherwise gathered or bunched together along the edges $104^a$, $106^a$, using known techniques in the art (e.g., fluting or corrugating laminator). Additionally, an elastic element $108^a$ such as an elastic band or strip, can be affixed to the cover sheet, such as depicted in FIGS. 23A and 23B, by attaching it by means of anchor stitches $110^a$ (e.g., stay stitches, surge stitches, etc.), by passing the elastic element $108^a$ through the cover sheet material directly (FIG. 23C) or through slits or openings $112^a$ (FIG. 23D), or by another known means of attachment. Referring to FIGS. 23E-F, 24 and 25 where the cover sheet $14^a$ is pleated or crimped, an elastic element $108^a$ can be anchored, for example, by adhesive or by stitching $110^a$ or other like attachment means. In use, when the tourniquet padding $10^a$ is wrapped around an extremity, the elastic element $108^a$ is stretched (arrow $114^a$) to provide an elasticized (expandable) band about the extremity and more securely maintain the padding in place on the extremity. Although not shown, an elastic element $108^a$ can also be used with the embodiments depicted in FIGS. 15-16.

Figure 26:
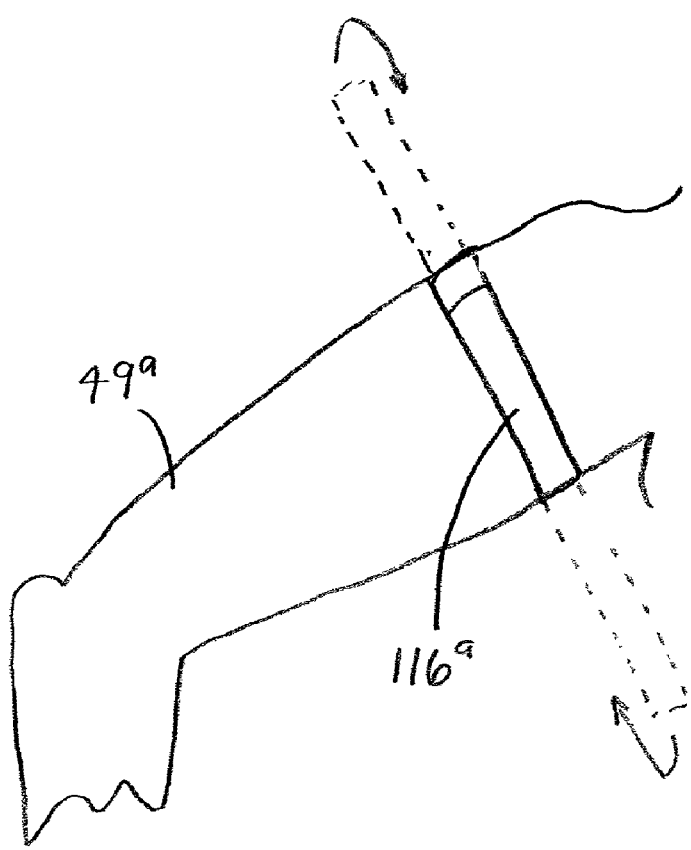
FIG. 26 is a front view of an elongate adhesive element wrapped around the upper arm of a person.

To further enhance the attachment of the various embodiments of the tourniquet padding of the invention, a double-sided adhesive strip or band $116^a$ (having a removable slip liner disposed on either side of the strip) can be utilized. As depicted in FIG. 26, the adhesive strip $116^a$ can be provided separately, the slip liner removed from a first side of the strip, and the strip $116^a$ wrapped about and applied to the extremity 49$^a$. The slip liner can then be removed from the second side of the strip, and the tourniquet padding then wrapped around the extremity over the adhesive strip 116$^a$, as in FIGS. 17A, 27A. The adhesive strip 116$^a$ can also be attached at an end 118$^a$, 120$^a$ (FIG. 19) or along the length (26, FIG. 1) to the outer side 24$^a$ (skin side) of the cover sheet 14$^a$ of the tourniquet padding. The adhesive band 116$^a$ can comprise a frictionally adhesive material, a pressure sensitive adhesive material, and the like.

In yet another embodiment shown in FIGS. 18A-19A, mating fastening members 122$^{a'}$ such as male/female snaps and the like, can be affixed along the proximal edge portion 56$^{a'}$ of the cover sheet 14$^{a'}$. As such, when the tourniquet padding 10$^{a'}$ is wrapped around an extremity, the fastening members can be joined to maintain a snug fit of the padding 10$^{a'}$. A series of fasteners can be used along one side to accommodate a range of circumferences of the various extremities to which the padding is applied.

The cover sheet 14$^a$ of the tourniquet padding 10$^a$ can comprise a material as described with respect to cover sheets 14, 16. In another embodiment, the cover sheet 14$^a$ comprises a polymeric film layer having anti-slip (cling) properties, strength, and elongation and memory properties such that the film layer will cling to skin and prevent slippage of a tourniquet disposed on the tourniquet padding during use on an extremity of a patient. The cover sheet 14$^a$ can comprise a single or multiple polymeric layers. At least one outside layer comprises a polymeric material having a moderate to high amount of cling. Desirably, the film cover layer 14$^a$ is a breathable film that allows the passage of vapor and gas there through. Breathable films are known in the art, and can be produced by any known method.

Examples of suitable polymer resins having inherent anti-slip properties for cling use include polyethylene and polyethylene-containing films, including conventional linear low density polyethylene (LDPE), very low density polyethylene (VLDPE), and ultralow density polyethylene (UL-DPE) resins, which are homopolymers, copolymers or terpolymers of ethylene and á-olefins such as propylene, 1-butene, 1-pentene, 1-hexene, 4-methyl-1-pentene, and 1-octene. Such polyethylene resins are known in the art, as described, for example, in U.S. Pat. No. 6,265,055 (Simpson et al.) and U.S. Pat. No. 6,171,681 (Mascarenhas et al.), the disclosures of which are incorporated by reference herein, and available commercially from a variety of sources, including, for example DOWLEX, AFFINITY, and ATTANE ethylene-1-octene copolymers (The Dow Chemical Co.), among others.

Tackifying or cling agents, as known in the art, can be added to the polymer resin mixture to provide or increase the cling of the cover sheet film layer 14$^a$. Examples of cling agents include hydrocarbon resins such as terpene resin, hydrogenated rosins, and rosin esters, atactic polypropylenes, polybutenes, polybutadiene, polyisobutylene, and the like. Such agents are described, for example, in U.S. Pat. No. 6,265,055 (Simpson et al.) and the patents cited therein (e.g., U.S. Pat. No. 5,922,441), the disclosures of which are incorporated by reference herein. Using a cling agent requires preblending or incorporating the agent into the resin material, and aging or the inclusion of an auxiliary component (e.g., alkali metal stearates, monoesters of fatty acids and polyols, such as glycerol mono-oleate or a sorbitan ester) to convey the cling agent to the film surface. Other disclosed cling agents include copolymers of ethylene and functional copolymers such as acrylates and vinyl acetate (U.S. Pat. No. 6,265,055 and cited patents, e.g., U.S. Pat. No. 5,212,001).

The cling film layer 14$^a$ can be combined with additional layers comprising a different polymer resin to provide mechanical strength and stretchability. For example, in a multi-layered construction, the sheet can comprise, for example, one or more outer layers of a highly stretchable cling film having a high amount of memory, and one or more inner or core layers of a low to moderate stretch film having a comparatively lower amount of memory.

The cling film 14$^a$ can also include one or more known and compatible additives. Examples of such additives include slip agents (e.g., oleic amide, stearic amide), anti-blocking agents (e.g., inorganic substance such as silica and talc) to reduce blocking when the films are wound up on reels, and allow smooth unwinding from the reels, antioxidants, pigments, colorants, and processing aids.

The film layer 14$^a$ is typically a blown film or cast film formed by a conventional extrusion process, or composite formed by a lamination process. Preferably, the gauge of the film is at least about 0.5 mil, preferably at least about 1 mil, up to about 3 mils, and is typically about 0.5 mil to about 2 mils.

To form the tourniquet padding 10$^a$ comprising a polymeric film cover layer 14$^a$, the film layer can be thermally bonded to a surface of a compressible padding layer 12$^a$, for example, by conveying the film layer and padding layer as a sandwich through a series of heaters and rolls that press the layers together to form a laminate. The film layer 14$^a$ can also be adhesively bonded to the padding layer 12$^a$, for example, using a pressure sensitive adhesive.

Optionally, adhesive elements 72$^a$ can be affixed to the surface of the film layer 14$^a$ to enhance the anti-slip properties of the film on the skin.

As depicted in FIG. 20, a slip sheet or liner 76$^a$ can be placed in contact with either surface of the tourniquet padding 10$^a$ to protect the exposed surface of the cover sheet 14$^a$ and to serve to prevent blocking of the padding 10$^a$ when in roll form. An example of a useful slip liner is a polycoated paper (coated with high density, moderate density, or low density polyethylene). The slip sheet 76$^a$ is removed prior to placement of the tourniquet padding 10$^a$ on the skin.

Figure 27A:
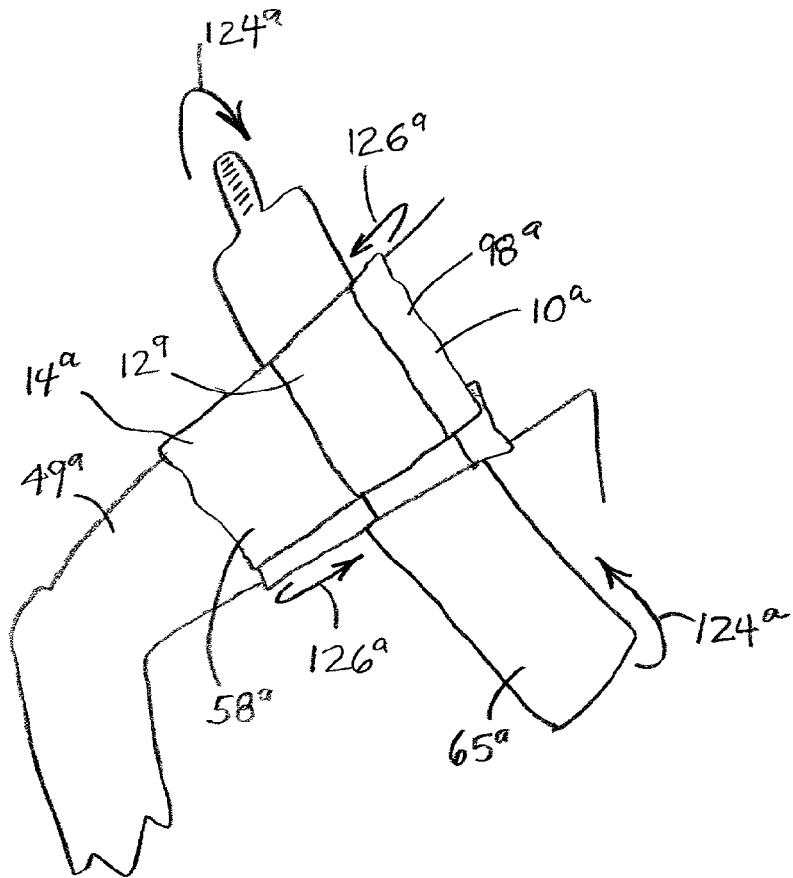
FIGS. 27A-27B are views of the tourniquet padding of FIG. 18 at sequential steps of applying the padding and a tourniquet onto the upper arm of a person.
Figure 27B:
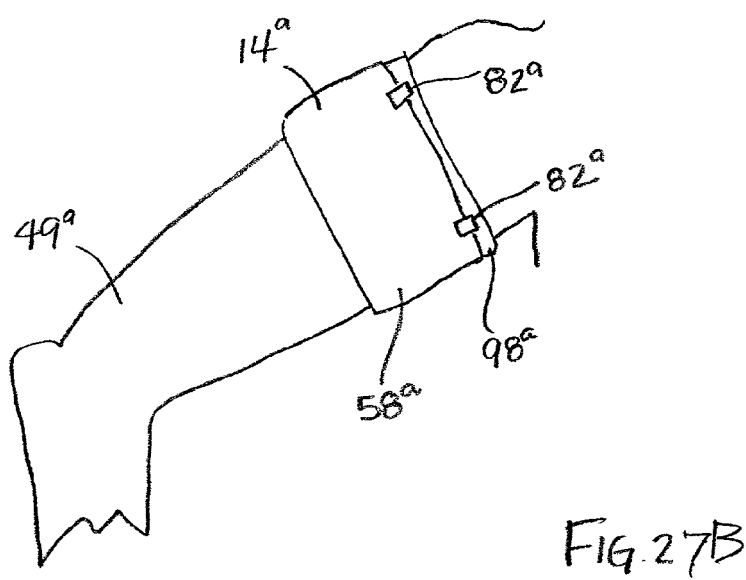

In use of the tourniquet padding 10$^a$ (FIGS. 18-20), the slip sheet 76$^a$ (if used) is removed, and the tourniquet padding 10$^a$ is wrapped about the limb, similar to that depicted in FIG. 17A, with the padding material 12$^a$ facing outward and the second surface of the cover sheet 14$^a$ placed against the skin. As shown in FIG. 27A, the tourniquet 65$^a$ is positioned on the padding 12$^a$ and wrapped about the extremity (arrows 124$^a$). As depicted, the cover sheet 14$^a$ can then be folded onto the tourniquet 65$^a$ (arrows 126$^a$) by turning the proximal flap portion 98$^a$ up onto the tourniquet 65$^a$, and the distal flap portion 58$^a$ folded onto the proximal portion 98$^a$ as shown in FIG. 27B (or vice versa). If desired, one or more adhesive elements 82$^a$ can be used to secure the ends of the cover sheet 14$^a$ over the tourniquet 65$^a$.

In the use of a tourniquet padding 10$^a$ utilizing a cling film cover sheet 14$^a$, the film side of the padding 10$^a$ is applied to the skin, a tourniquet 65$^a$ positioned onto the padding 12$^a$, and the flap portions 58$^a$, 98$^a$ are folded onto the tourniquet 65$^a$ with the ends overlapping, preferably in a self-adhering connection due to the cling properties of the film. Optionally, one or more adhesive elements 82$^a$ can be used to secure the flaps 58$^a$, 98$^a$ of the cover sheet 14$^a$.

The invention has been described by reference to detailed examples and methodologies. These examples are not meant to limit the scope of the invention. It should be understood that variations and modifications may be made while remaining within the spirit and scope of the invention, and the invention is not to be construed as limited to the specific embodiments shown in the drawings.

What is claimed:

1. A tourniquet padding, comprising:
    a single unitary cover sheet having an inner surface, an outer surface, a length, opposing edges along the length, and a plurality of discrete and spaced apart adhesive elements having anti-slip properties situated on the outer surface of the cover sheet; and
    a padding material situated on a portion of the inner surface of the cover sheet and extending the length of the cover sheet between said opposing edges, the padding material having a length and width sized for receiving a tourniquet thereon, and the cover sheet extending the length of the padding material; and
    the cover sheet having a width sufficient such that with the tourniquet situated over the padding material, the cover sheet can be placed to substantially cover the tourniquet.

2. The tourniquet padding of claim 1, wherein the adhesive elements are frictionally adhesive.

3. The tourniquet padding of claim 2, wherein the adhesive elements comprise a material selected from the group consisting of latex rubber, silicon rubber, and polyvinyl chloride.

4. The tourniquet padding of claim 1, wherein the adhesive elements comprise a biocompatible adhesive material that is adherable to skin.

5. The tourniquet padding of claim 1, further comprising a slip sheet releasably attached to the adhesive elements on the cover sheet.

6. The tourniquet padding of claim 1, wherein the length of the cover sheet is sufficient to be wrapped around an extremity of a person.

7. The tourniquet padding of claim 1, wherein the cover sheet comprises a non-woven material.

8. The tourniquet padding of claim 1, wherein the cover sheet comprises a material selected from the group consisting of paper, reinforced scrim material, crepe, cloth, terry cloth, cheesecloth, plastic, and combinations thereof.

9. The tourniquet padding of claim 1, wherein the cover sheet comprises a polymer film material.

10. The tourniquet padding of claim 1, wherein the cover sheet comprises a stretch cling plastic material.

11. The tourniquet padding of claim 1, wherein the cover sheet comprises a laminate selected from the group consisting of a laminate of tissue and a non-woven material, a laminate of tissue and a woven material, a laminate of a polymer film and a non-woven or woven material, and a laminate of a polyurethane foam and a polymer film.

12. The tourniquet padding of claim 1, wherein the cover sheet comprises a breathable material.

13. The tourniquet padding of claim 1, wherein at least the outer surface of the cover sheet comprises a liquid-repellent material.

14. The tourniquet padding of claim 1, wherein the distal edge portion of the cover sheet comprises perforations, slits, or a combination thereof, to separate the edge portion into sections.

15. The tourniquet padding of claim 1, further comprising a slip sheet releasably attached to the adhesive elements on the cover sheet.

16. The tourniquet padding of claim 1, wherein the proximal edge portion of the cover sheet is gathered.

17. The tourniquet padding of claim 16, wherein the proximal edge portion of the cover sheet is pleated or crimped.

18. The tourniquet padding of claim 16, wherein the cover sheet further comprises an elastic element attached to the proximal edge portion.

19. The tourniquet padding of claim 1, wherein at least one of the distal edge portion and the proximal edge portion have a width sufficient for covering a tourniquet positioned over the padding material of the tourniquet padding.

20. The tourniquet padding of claim 1, further comprising an adhesive member for securing the proximal and distal edge portions together.

21. The tourniquet padding of claim 1, further comprising one or more adhesive elements attached to at least a portion of the outer surface of the cover sheet, the adhesive element having a length sufficient to be wrapped around an extremity of a person.

22. The tourniquet padding of claim 1, wherein the cover sheet comprises one or more perforated lines.

23. The tourniquet padding of claim 1, wherein the padding material comprises cast padding.

24. The tourniquet padding of claim 1, wherein the padding material comprises a foam material.

25. The tourniquet padding of claim 1, wherein the cover sheet comprises a folded unitary sheet with the padding material sandwiched therebetween.

26. The tourniquet padding of claim 1, wherein the padding material comprises a porous material.

27. The tourniquet padding of claim 1, wherein the padding material comprises a natural material, a synthetic material, or a combination thereof.

28. The tourniquet padding of claim 1, wherein the padding material comprises a material selected from the group consisting of cotton, nylon, rayon, acrylic, polyester, polyurethane, paper, and combinations thereof.

29. The tourniquet padding of claim 1, wherein the cover sheet comprises a material selected from the group consisting of paper, reinforced scrim material, crepe, cloth, terry cloth, cheesecloth, plastic, and combinations thereof.

30. A tourniquet padding, comprising:
    a single unitary cover sheet having an inner surface, an outer surface, a length, and opposing edges along the length; the cover sheet comprising a polymer film material, and at least the outer surface of the cover sheet having a plurality of discrete and spaced apart adhesive elements with anti-slip properties situated thereon; and
    a padding material situated on a portion of the inner surface of the cover sheet and extending the length of the cover sheet between said opposing edges, the padding material having a length and width sized for receiving a tourniquet thereon, and the cover sheet extending the length of the padding material; and
    the cover sheet having a width sufficient such that with the tourniquet situated over the padding material, the cover sheet can be placed to substantially cover the tourniquet.

31. The tourniquet padding of claim 30, wherein the cover sheet comprises a stretch cling plastic material.

32. The tourniquet padding of claim 30, wherein the polymer film material is a breathable material.

33. A tourniquet padding, comprising:
    a single unitary cover sheet having an inner surface, an outer surface, a length, and opposing edges along the length, the cover sheet comprising a plurality of spaced apart and discrete adhesive elements situated on the outer surface of the cover sheet to provide anti-slip properties, and an adhesive element on the inner surface along at least one of said edges; and a padding material situated on a portion of the inner surface of the cover sheet and extending the length of the cover sheet between said opposing edges, the padding material having a length and width sized for receiving a tourniquet thereon, and the cover sheet extending the length of the padding material; and the cover sheet having a width sufficient such that with the tourniquet situated over the padding material, the cover sheet can be placed to substantially cover the tourniquet with said opposing edges overlapped.

34. The tourniquet padding of claim 33, wherein at least one of the adhesive elements is frictionally adhesive.

35. The tourniquet padding of claim 33, wherein one or more adhesive elements are attached to at least a portion of the outer surface of the cover sheet, the adhesive element having a length sufficient to be wrapped around an extremity of a person.

36. The tourniquet padding of claim 35, wherein the second cover sheet can be frictionally adhered to the skin of the person.

37. A padding for a tourniquet, comprising:

a cover sheet comprising an inner surface and an outer surface, a plurality of spaced apart and discrete adhesive elements with anti-slip properties situated on said outer surface of the plastic film layer; the cover sheet having a width such that a portion of the cover sheet may be folded over a distal edge of a tourniquet when situated on the cover sheet; and a pad comprising a compressible material having memory situated on the inner surface of the cover sheet, the pad having a length, and the cover sheet extending the length of the pad.

38. The tourniquet padding of claim 37, wherein the pad is adhesively attached to the cover sheet.

39. The tourniquet padding of claim 37, wherein when the padding is wrapped about and adhered to a limb of a person, at least the distal portion of the padding is not adhered to the limb and may lift upward when a tourniquet situated on the padding is inflated.

40. The padding of claim 37, wherein the pad is exposed on the surface of the cover sheet.

* * * * *